United States Patent [19]
Suzuki et al.

[11] Patent Number: 5,921,975
[45] Date of Patent: Jul. 13, 1999

[54] ABSORBENT ARTICLE HAVING ANTILEAKAGE WALLS

[75] Inventors: Youichi Suzuki; Reiko Konno; Yasuo Toyoshima; Minoru Nakanishi, all of Tochigi-ken, Japan

[73] Assignee: Kao Corporation, Tokyo, Japan

[21] Appl. No.: 08/921,373

[22] Filed: Aug. 29, 1997

Related U.S. Application Data

[63] Continuation of application No. 08/579,263, Dec. 27, 1995, abandoned.

[30] Foreign Application Priority Data

| Dec. 27, 1994 | [JP] | Japan | 6-326367 |
| Feb. 23, 1995 | [JP] | Japan | 7-035155 |
| Feb. 23, 1995 | [JP] | Japan | 7-035156 |
| Apr. 17, 1995 | [JP] | Japan | 7-091160 |

[51] Int. Cl.⁶ ................................................. A61F 13/15
[52] U.S. Cl. ........................................ 604/385.2; 604/387
[58] Field of Search .................................. 604/385.1–390

[56] References Cited

U.S. PATENT DOCUMENTS

| Re. 33,106 | 11/1989 | Beckestrom | 604/385.2 |
| 3,860,004 | 1/1975 | Nystrand | 604/389 |
| 4,623,342 | 11/1986 | Ito et al. | 604/385.2 |
| 4,770,657 | 9/1988 | Ellis et al. | 604/385.2 |
| 4,883,482 | 11/1989 | Gandrez et al. | 604/385.2 |
| 5,074,856 | 12/1991 | Coe et al. | 604/385.2 |
| 5,167,653 | 12/1992 | Igaez et al. | 604/385.2 |
| 5,234,422 | 8/1993 | Sneller et al. | 604/385.2 |
| 5,275,590 | 1/1994 | Huffmin et al. | 604/385.2 |
| 5,304,159 | 4/1994 | Tanji et al. | 604/385.2 |
| 5,342,342 | 8/1994 | Kitaoka | 604/385.2 |
| 5,387,210 | 2/1995 | Murakami | 604/385.1 |
| 5,447,507 | 9/1995 | Yamamoto | 604/385.2 |
| 5,454,804 | 10/1995 | Widlund | 604/387 |
| 5,490,847 | 2/1996 | Correa et al. | 604/387 |
| 5,542,941 | 8/1996 | Morita | 604/387 |

FOREIGN PATENT DOCUMENTS

| 5552758 | 4/1980 | Japan | 604/385.1 |
| 603491 | 1/1985 | Japan . | |
| 6019693 | 6/1985 | Japan . | |
| 5220191 | 8/1993 | Japan | 604/387 |
| 2244653 | 12/1991 | United Kingdom | 604/387 |
| 3010733 | 6/1993 | WIPO | 604/386 |

*Primary Examiner*—Mark O. Polutta
*Attorney, Agent, or Firm*—Birch, Stewart, Kolasch & Birch, LLP

[57] ABSTRACT

An absorbent article having a central absorbent body comprising a liquid permeable topsheet, a liquid impermeable backsheet and an absorbent member interposed between the topsheet and the backsheet, and a pair of flaps provided in the opposing longitudinal sides of the central absorbent body, is characterized in that:

each of the flaps is connected with the surface of the absorbent article which, in use, does not contact the skin of the wearer, each of the flaps forms an antileakage wall along each edge of the opposing longitudinal sides of the central absorbent body, each of the flaps is folded outwardly from the central absorbent body to form an antileakage surface, and the antileakage surface in the portion which contacts the discharging portion of the wearer in use is a surface substantially parallel to the skin-contacting surface of the absorbent article.

16 Claims, 17 Drawing Sheets

ABSORBENT ARTICLE HAVING ANTILEAKAGE WALLS

This application is a continuation of application Ser. No. 08/579,263 filed on Dec. 27, 1995, now abandoned.

BACKGROUND OF THE INVENTION

This invention relates to an absorbent article, such as a sanitary napkin, which is to be put on a wearer and contacted with the skin in order to absorb body fluids. This invention particularly relates to an absorbent article having good performance for preventing leakage on both sides of the absorbent article.

Various absorbent articles, such as paper diapers and sanitary napkins, have heretofore been proposed and used in practice. However, the conventional absorbent articles have the drawbacks that they often soil clothes of the wearer due to leakage on both sides of the absorbent article and thus give an unpleasant feel to the wearer. Therefore, various attempts have heretofore been made in order to eliminate such drawbacks.

For example, it has been proposed to form antileakage walls on opposing longitudinal sides of an absorbent article. Also, it has been proposed to shape the absorbent article itself so as to correspond to the shape of the wearing portion of the wearer. Further, it has been proposed to locate elastic members in an absorbent article in such a manner that the absorbent article follows up a change in shape in use. Specifically, in Japanese Utility Model Publication 60-19693, an absorbent article is proposed in which flaps formed by sealing a topsheet and a backsheet on opposing longitudinal sides are folded toward the surface of the absorbent article. Also, in Japanese Patent Publication 60-3491, an absorbent article is proposed in which flaps formed by sealing a topsheet and a backsheet on opposing longitudinal sides are folded toward the surface of the absorbent article and are thereafter folded outwardly.

With the conventional absorbent articles described above, in the use condition, in which the discharging portion of the wearer is located in the central portion of an absorbent member of the absorbent article, and the underwear is put on the wearer in close contact with the wearer's body, leakage from the absorbent member can be reduced. However, with the conventional absorbent articles described above, leakage cannot be restricted perfectly. In particular, in the actual use, the use condition of the absorbent article is not always kept in the use condition described above. For example, the absorbent article is often used with the discharging portion of the wearer being shifted in position from the central portion of the absorbent member. Also, the absorbent article in use cannot follow up complicated forms occurring due to movement of the wearer, and a gap occurs between the absorbent article and the wearing portion of the wearer. In such cases, with the conventional absorbent articles described above, leakage preventing effects satisfactory to the wearer cannot be obtained.

Further, with the conventional absorbent articles described above, front and rear ends of each of the folded flaps are adhered to the absorbent article in front and rear end portions of the absorbent article. Therefore, the fitting performance in the portion, which contacts the discharging portion of the wearer in use, is not sufficient, and leakage still occurs on both sides of the absorbent article.

SUMMARY OF THE INVENTION

Therefore, an object of the present invention is to provide an absorbent article, which has good fitting performance with respect to the wearer in use and has little risk of leakage on both sides of the absorbent article.

The inventors carried out extensive research in order to eliminate the problems described above and found that the object can be accomplished with an absorbent article provided with flaps having a specific shape.

The present invention is based on the findings described above. The present invention provides an absorbent article having a central absorbent body comprising a liquid permeable topsheet, a liquid impermeable backsheet and an absorbent member interposed between the topsheet and the backsheet, and a pair of flaps provided in the opposing longitudinal sides of the central absorbent body, the absorbent article being characterized in that:

each of the flaps is connected with the surface of the absorbent article which, in use, does not contact the skin of the wearer, each of the flaps forms an antileakage wall along each edge of the opposing longitudinal sides of the central absorbent body, each of the flaps is folded outwardly from the central absorbent body to form an antileakage surface, and the antileakage surface in the portion which contacts the discharging portion of the wearer in use is a surface substantially parallel to the skin-contacting surface of the absorbent article.

The absorbent article in accordance with the present invention has good fitting performance in the portion, which contacts the discharging portion of the wearer in use. The absorbent article in accordance with the present invention also has little risk of leakage on both sides of the absorbent article. Specifically, the effects described in (1) through (9) below can be obtained.

(1) A side pocket is formed between each of the flaps and the central absorbent body. Therefore, even if body fluids flow along the surface of the topsheet, they can be prevented from passing over each of the flaps and leaking.

(2) Each of the antileakage surfaces can be formed at a position higher than the surface of the absorbent article which, in use, contacts the skin of the wearer. Therefore, even if the absorbent member is twisted and becomes thick, the fitting performance can be prevented from becoming bad.

(3) Each of the antileakage surfaces spreads along the skin of the wearer in use, and each of the flaps does not become folded over the absorbent member. Therefore, the side pockets can be formed reliably.

(4) Because the antileakage surfaces spread along the skin of the wearer, the members constituting the absorbent article do not become localized in the thickness direction of the absorbent member, and twist of the absorbent member can be restricted.

(5) Leakage can be restricted by each of the antileakage walls and each of the antileakage surfaces.

(6) The spread of the flaps with respect to the skin of the wearer can be promoted by the antileakage surfaces, the fitting performance with respect to the skin can be enhanced, and a feeling of physical discomfort given to the wearer can be reduced.

(7) Instead of each of the flaps being secured in the front and rear edge portions, each of the flaps may be released outwardly in the front and rear edge portions to form a substantially flat surface-like shape. In such cases, by the effects of each of the released flaps, the shape of the antileakage surface, which is substantially parallel to the skin-contacting surface of the absorbent article, and the side pocket formed by each of the antileakage walls can be formed and kept reliably.

(8) In cases where the absorbent article is provided with wing portions, the absorbent article can be firmly secured to shorts, or the like, in use by the wing portions, and the absorbent article undergoes little slipping-off during the use.

(9) Since the materials constituting the absorbent article do not become localized, local concentration of force does not occur during the use, and the absorbent article does not easily twist.

The absorbent article in accordance with the present invention is useful particularly for sanitary napkins and disposable diapers.

DETAILED DESCRIPTION OF THE INVENTION

Firstly, first to sixth embodiments of the absorbent article in accordance with the present invention will be described hereinbelow with reference to the accompanying drawings.

Figure 1:
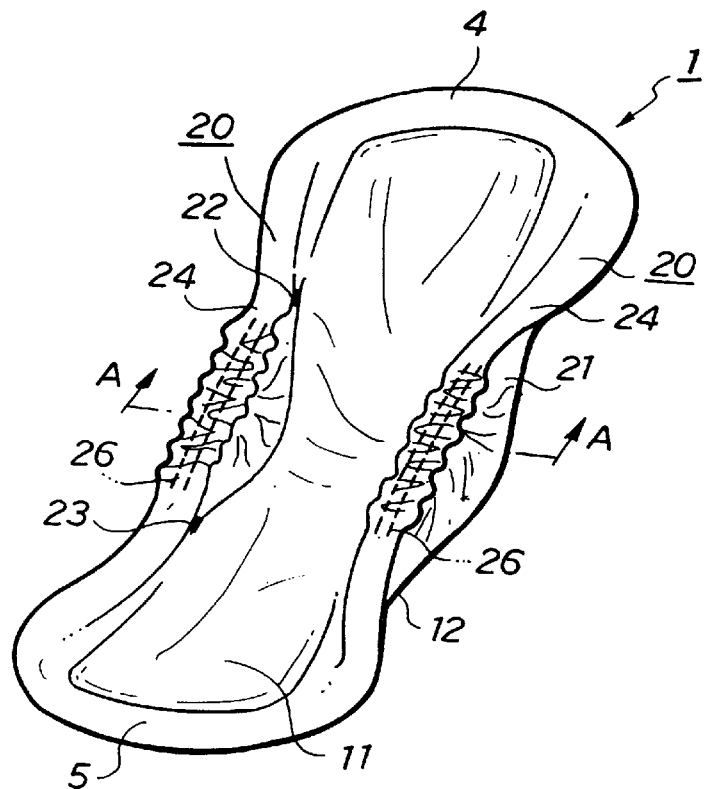
FIG. 1 is a perspective view showing a first embodiment of the absorbent article in accordance with the present invention, which is constituted as a sanitary napkin.
Figure 2:
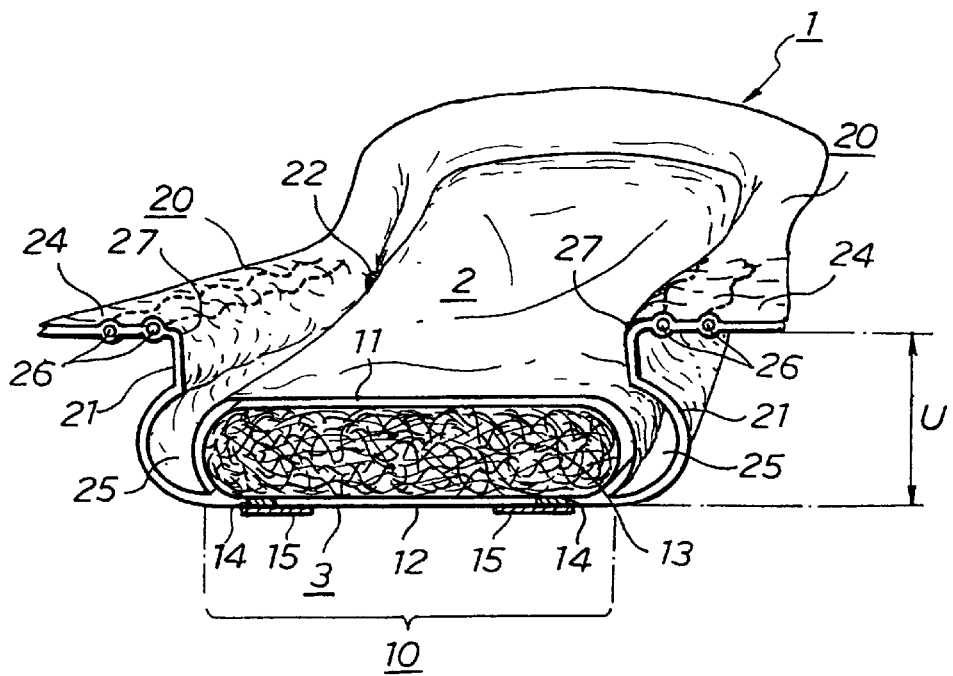
FIG. 2 is a perspective sectional view taken along line A—A of FIG. 1.
Figure 3:
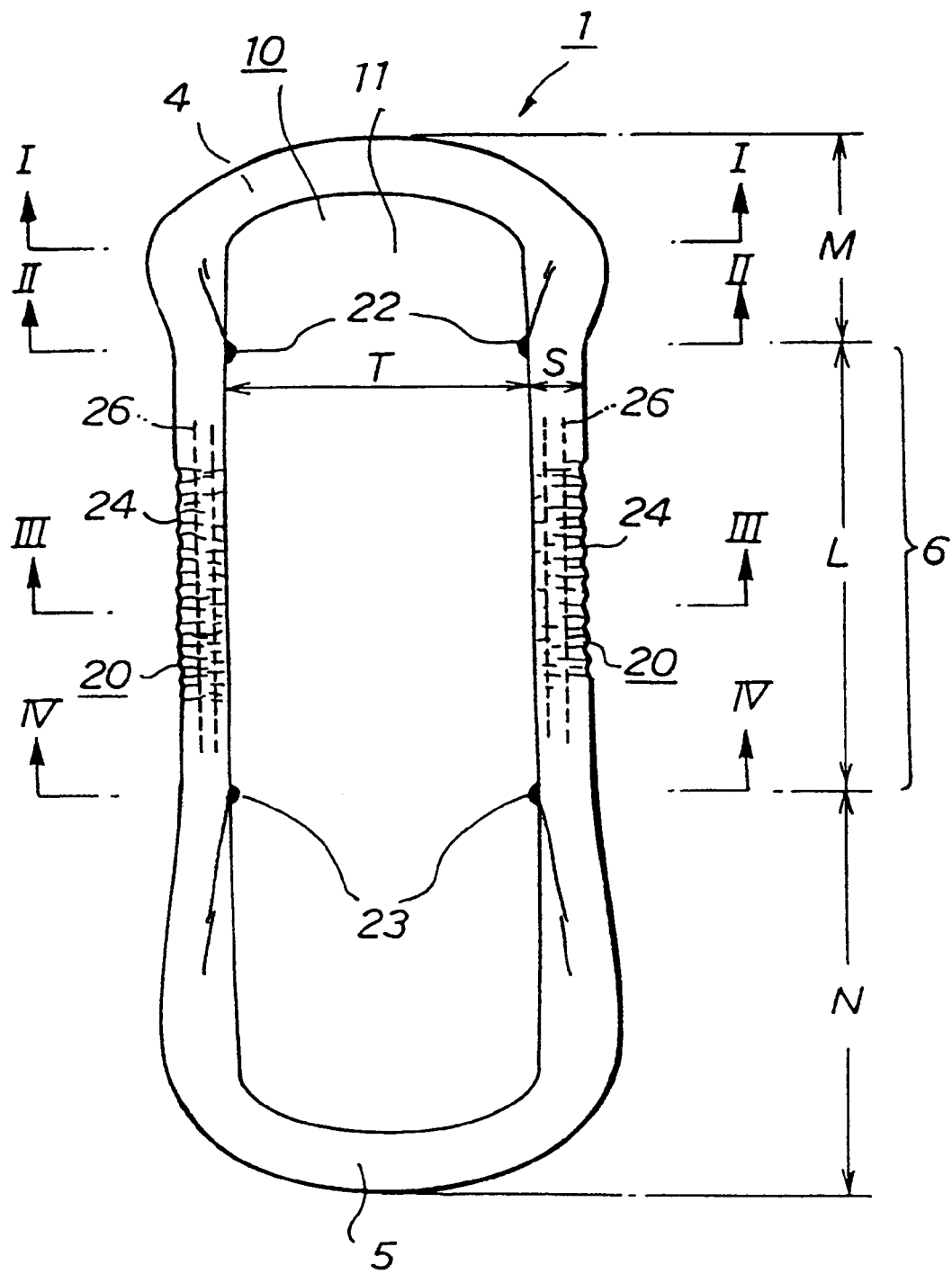
FIG. 3 is a plan view showing the sanitary napkin of FIG. 1.
Figure 4A:
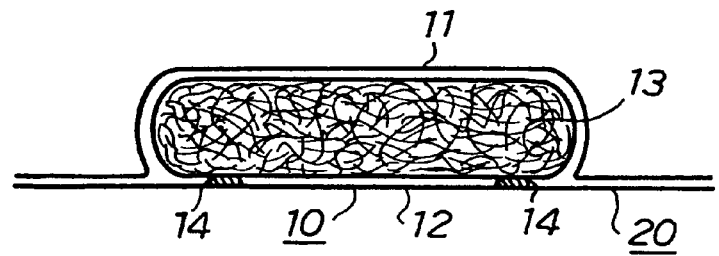
FIG. 4A is a schematic sectional view taken along line I—I of FIG. 3.
Figure 4B:
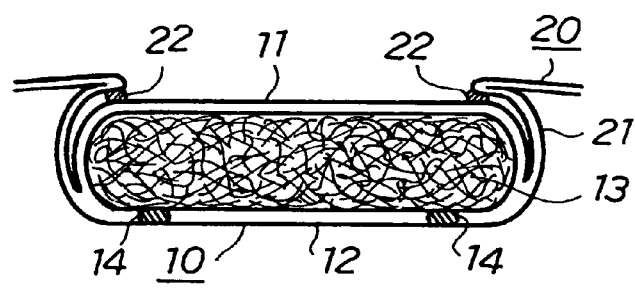
FIG. 4B is a schematic sectional view taken along line II—II of FIG. 3.
Figure 4C:
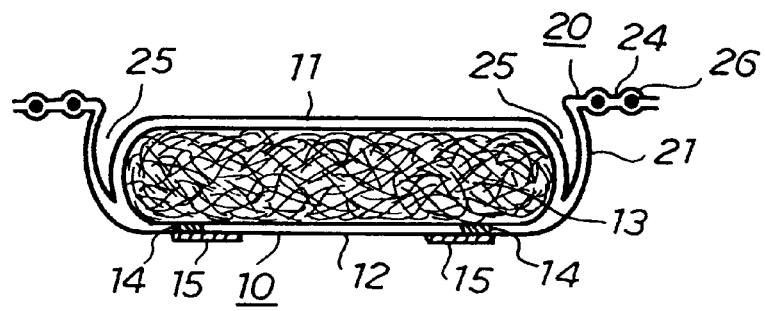
FIG. 4C is a schematic sectional view taken along line III—III of FIG. 3.
Figure 4D:
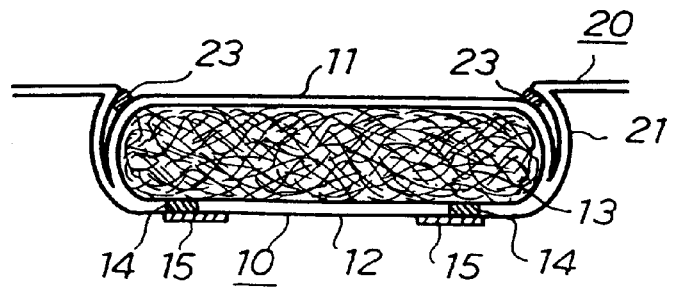
FIG. 4D is a schematic sectional view taken along line IV—IV of FIG. 3.

FIG. 1 is a perspective view showing a first embodiment of the absorbent article in accordance with the present invention, which is constituted as a sanitary napkin. FIG. 2 is a perspective sectional view taken along line A—A of FIG. 1 (the perspective view showing the cross section of the sanitary napkin, which is taken along the width direction in the central portion with respect to the longitudinal direction, and showing the portion of the sanitary napkin forward from the cross section). In FIG. 2, the sectional shape is shown schematically. FIG. 3 is a plan view showing the sanitary napkin of FIG. 1. FIGS. 4A, 4B, 4C, and 4D are schematic sectional views showing the sanitary napkin of FIGS. 1 and 3. FIG. 4A is a schematic sectional view taken along line I—I of FIG. 3. FIG. 4B is a schematic sectional view taken along line II—II of FIG. 3. FIG. 4C is a schematic sectional view taken along line III—III of FIG. 3. FIG. 4D is a schematic sectional view taken along line IV—IV of FIG. 3.

The first embodiment of the sanitary napkin has a central absorbent body comprising a liquid permeable topsheet, a liquid impermeable backsheet and an absorbent member interposed between the topsheet and the backsheet. Also, the sanitary napkin has a pair of flaps provided in the opposing longitudinal sides of the central absorbent body. Each of the flaps is connected with the surface of the absorbent article which, in use, does not contact the skin of the wearer. Also, each of the flaps forms an antileakage wall along each edge of the opposing longitudinal sides of the central absorbent body. Further, each of the flaps is folded outwardly from the central absorbent body to form an antileakage surface. The antileakage surface in the portion which contacts the discharging portion of the wearer in use is a surface substantially parallel to the surface of the absorbent article which, in use, contacts the skin of the wearer. Furthermore, the antileakage wall is formed by folding each of the flaps toward the topsheet of the central absorbent body and is secured to the central absorbent body in a front portion that is forward from the portion which contacts the discharging portion of the wearer in use, and in a rear portion that is rearward from the portion which contacts the discharging portion of the wearer in use.

Specifically, as illustrated in FIGS. 1, 2, 3, and 4A through 4D, a sanitary napkin 1 has a central absorbent body 10 comprising a liquid permeable topsheet 11, a liquid impermeable backsheet 12 and an absorbent member 13 interposed between the topsheet 11 and the backsheet 12. Also, the sanitary napkin has a pair of flaps 20, 20 provided in the opposing longitudinal sides of the central absorbent body. Such a structure is similar to the structure of an ordinary sanitary napkin.

In the first embodiment of the sanitary napkin 1, each of the topsheet 11 and the backsheet 12 has an extended portion and is thereby formed to be larger as a whole than the absorbent member 13. Each of the flaps 20, 20 is formed by sealing the extended portion of the topsheet 11 and the extended portion of the backsheet 12 together. Also, a front edge portion 4 and a rear edge portion 5 are thereby formed. The sealing of the extended portion of the topsheet 11 and the extended portion of the backsheet 12 may be carried out with an ordinary technique, such as heat sealing or an adhesive agent technique.

As illustrated in FIGS. 2 and 4A through 4D, the absorbent member 13 is secured to the backsheet 12 via absorbent member fixing agents 14, 14.

Also, slipping-off preventing agents 15, 15 are provided on a surface 3 of the sanitary napkin 1 which, in use, does not contact the skin of the wearer (hereinafter referred to as "skin-uncontacting surface") at the central absorbent body 10 of the sanitary napkin 1. The slipping-off preventing agents 15, 15 serve to adhere the sanitary napkin 1 to shorts when the sanitary napkin 1 is used.

As the materials for forming the topsheet 11 and the backsheet 12, any of materials, which are ordinarily used as topsheets and backsheets of absorbent articles, such as sanitary napkins, may be employed.

Also, as the absorbent member 13, any of known absorbent members, which are constituted of pulp and highly absorbent polymers, may be employed.

Further, as the absorbent member fixing agents 14, 14 and the slipping-off preventing agents 15, 15, any of adhesive agents ordinarily used for absorbent articles, such as sanitary napkins, may be employed.

As illustrated in FIGS. 1, 2, and 3, in the first embodiment of the sanitary napkin 1, each of the flaps 20, 20 is connected with the skin-uncontacting surface 3 of the sanitary napkin 1. Also, each of the flaps 20, 20 is folded toward the topsheet 11 of the central absorbent body 10 to form an antileakage wall 21 along each edge of the opposing longitudinal sides of the central absorbent body 10. Further, each of the flaps 20, 20 is folded outwardly from the central absorbent body 10 to form an antileakage surface 24. Furthermore, each of the antileakage walls 21, 21 is secured to the central absorbent body 10 in the front portion that is forward from a portion 6 which, in use, contacts the discharging portion of the wearer and in the rear portion that is rearward from the portion 6 which, in use, contacts the discharging portion of the wearer. Each of the antileakage surfaces 24, 24 in the portion 6 which, in use, contacts the discharging portion of the wearer is formed as a surface substantially parallel to the skin-contacting surface 2 of the central absorbent body 10, which surface 2, in use, contacts the skin of the wearer.

More specifically, as illustrated in FIGS. 2 and 4A through 4D, the topsheet 11 covers each of the side surfaces of the absorbent member 13, and the extended portion of the topsheet 11 is sealed with the extended portion of the backsheet 12. Each of the flaps 20, 20, which is formed by the extended portion of the topsheet 11 and the extended portion of the backsheet 12 having been sealed together, is thereby connected with the skin-uncontacting surface 3.

Also, as illustrated in FIGS. 2 and 4A through 4D, each of the flaps 20, 20 is folded at each side edge of the central absorbent body 10 to form each of the antileakage walls 21, 21. Further, as illustrated in FIGS. 2 and 4B through 4D, each of the flaps 20, 20 is folded outwardly from the central absorbent body 10 at a position slightly upper than the level of the skin-contacting surface 2 of the sanitary napkin 1 in order to form each of the antileakage surfaces 24, 24.

As illustrated in FIGS. 1, 3, and 4B, in the front portion that is forward from the portion 6 which, in use, contacts the discharging portion of the wearer, the antileakage walls 21, 21 are secured to the topsheet 11 of the central absorbent body 10 via fixing portions 22, 22 in the front portion. Also, as illustrated in FIGS. 1, 3, and 4D, in the rear portion that is rearward from the portion 6 which, in use, contacts the discharging portion of the wearer, the antileakage walls 21, 21 are secured to the topsheet 11 of the central absorbent body 10 via fixing portions 23, 23 in the rear portion.

The expression "a portion which, in use, contacts the discharging portion of the wearer" as used herein means a portion of the surface of the sanitary napkin, which portion contacts the discharging portion of the wearer when the sanitary napkin is used (hereinafter this portion is referred to as "contacting portion"). Specifically, the contacting portion is the portion located between the fixing portions 22, 22 and the fixing portions 23, 23 with respect to the longitudinal direction of the sanitary napkin. Also, the term "front portion" as used herein means the entire portion, which is forward from the contacting portion 6 (i.e., forward as viewed from the wearer) and includes the front edge portion 4. The term "rear portion" as used herein means the entire portion, which is rearward from the contacting portion 6 (i.e., rearward as viewed from the wearer) and includes the rear edge portion 5.

The fixing portions 22, 22 and the fixing portions 23, 23 can be formed easily by using an adhesive, or the like, ordinarily used for absorbent articles or by a heat sealing technique.

As illustrated in FIGS. 2 and 4C, since the antileakage walls 21, 21 are secured to the topsheet 11 of the central absorbent body 10 in the manner described above, each of side pockets 25, 25 is formed between each antileakage wall 21 and the central absorbent body 10 in the contacting portion 6. Also, as illustrated in FIGS. 2, 3, and 4C, since the antileakage walls 21, 21 are secured to the topsheet 11 of the central absorbent body 10 in the manner described above, each of the antileakage surfaces 24, 24 in the contacting portion 6 is formed as the surface substantially parallel to the skin-contacting surface 2 of the central absorbent body 10 and at the position slightly upper than the level of the skin-contacting surface 2.

Further, as illustrated in FIGS. 1, 2, 3, and 4A through 4D, in the first embodiment of the sanitary napkin 1, each of the flaps 20, 20 is not heat sealed in the front edge portion 4 and the rear edge portion 5. Instead, in the portion forward from the fixing portions 22, 22 in the front portion (i.e., in the portion which is located on the front side of the wearer when the sanitary napkin is used), the aforesaid folded condition of the flap 20 is released gradually toward the front side in such a manner that the flap 20 takes a substantially flat surface-like shape. Similarly, in the portion rearward from the fixing portions 23, 23 in the rear portion (i.e., in the portion which is located on the rear side of the wearer when the sanitary napkin is used), the aforesaid folded condition of the flap 20 is released gradually toward the rear side in such a manner that the flap 20 takes a substantially flat surface-like shape. In cases where the flap 20 is formed in this manner, the shape of the antileakage surface 24, which is substantially parallel to the skin-contacting surface 2, and the side pocket 25 can be formed and kept reliably.

In the first embodiment of the sanitary napkin 1, the length L of the contacting portion 6 should preferably fall within the range of 3 to 20 cm, and should more preferably fall within the range of 5 to 15 cm. Also, in the sanitary napkin 1, the length M of the front portion, which is forward from the fixing portions 22, 22, should preferably fall within the range of 0 to 10 cm, and should more preferably fall within the range of 2 to 8 cm. Further, in the sanitary napkin 1, the length N of the rear portion, which is rearward from the fixing portions 23, 23, should preferably fall within the range of 3 to 25 cm, and should more preferably fall within the range of 5 to 18 cm.

The width S of each antileakage surface 24 in the contacting portion 6 (shown in FIG. 3) should preferably fall within the range of 0.5 to 4 cm, and should more preferably fall within the range of 0.7 to 2.5 cm. If the width S of each antileakage surface 24 is smaller than 0.5 cm, it will often occur that the antileakage wall 21 falls down to the central absorbent body 10, and the side pocket 25 is not formed. If the width S of each antileakage surface 24 is larger than 4 cm, it will often occur that the flat surface-like shape of the antileakage surface 24 cannot be kept easily, and leakage is induced. Therefore, the width S of each antileakage surface 24 should preferably fall within the aforesaid range.

The height U of the antileakage surface 24, as measured from the skin-uncontacting surface 3, (shown in FIG. 2) should preferably be at most 40 mm, and should more preferably fall within the range of 5 to 25 mm.

The width T between the antileakage surfaces 24 and 24 in the contacting portion 6 (shown in FIG. 3) should preferably be at least 30 mm so that the antileakage surfaces 24, 24 may not cover the skin-contacting surface 2 of the central absorbent body 10.

With the first embodiment of the sanitary napkin 1 having the structure described above, the antileakage surfaces 24, 24 can appropriately fit to the skin of the wearer, and leakage on both sides can be prevented effectively. Specifically, since the side pockets 25, 25 are formed, a discharged liquid flowing along the surface of the topsheet 11 flows into the side pockets 25, 25 and is thereafter absorbed by the absorbent member 13 from the side surfaces of the central absorbent body 10. Therefore, leakage on both sides can be prevented effectively.

Furthermore, the first embodiment of the sanitary napkin 1 is provided with elastic members 26, 26, which are located in each of the antileakage surfaces 24, 24 in the contacting portion 6.

By the provision of the elastic members 26, 26, the shape of the antileakage wall 21 can be kept appropriately. Also, by the provision of the elastic members 26, 26, the shape of the antileakage surface 24, which is substantially parallel to the skin-contacting surface 2 of the central absorbent body 10, can be kept appropriately, and the fitting performance with respect to the wearer can be enhanced. Further, since the elastic members 26, 26 are provided in the antileakage surface 24 (on the side outward from a folding line 27 shown in FIG. 2), the shape of the side pocket 25 can be kept large, and therefore leakage on both sides can be prevented effectively.

As the elastic member 26, any of elastic members ordinarily used for absorbent articles may be employed. Examples of particularly preferable materials for the elastic member 26 include foamed materials of polyolefins and polyurethanes, and natural rubber. The elastic member 26 may take on various forms, such as string-like, film-like, and flat surface-like shapes. In this embodiment, string-like elastic members are employed. Also, no limitation is imposed on the number of the elastic members 26, 26, . . . However, in cases where the elastic members 26, 26, . . . take on the form of a string, from the viewpoint of shape keeping and prevention of leakage on both sides, it is effective to provide at least two elastic members 26, 26.

Further, the elastic member 26 should preferably have such an elastic force that the stress at 20% elongation of the flap 20 provided with the elastic members 26, 26 may be at most 100 g.

The second, third, fourth, and fifth embodiments of the absorbent article in accordance with the present invention will be described hereinbelow with reference to FIGS. 5, 6, 7, and 8.

Figure 5:
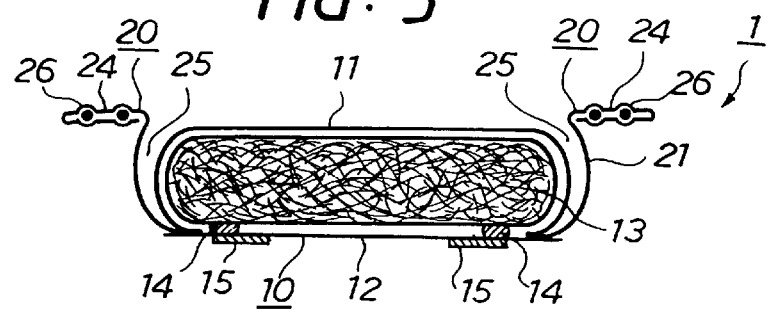
FIG. 5 is a sectional view showing a second embodiment of the absorbent article in accordance with the present invention, which is constituted as a sanitary napkin, the view corresponding to FIG. 4C.
Figure 6:
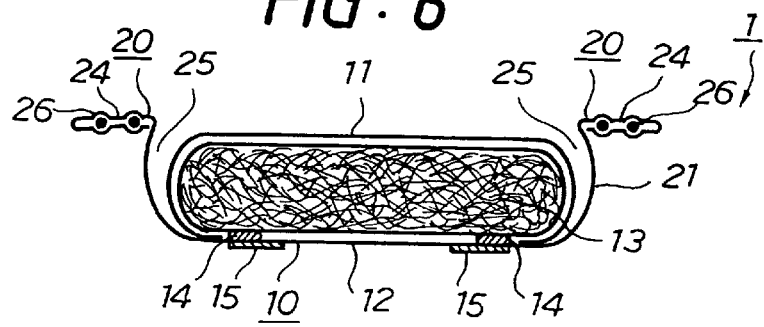
FIG. 6 is a sectional view showing a third embodiment of the absorbent article in accordance with the present invention, which is constituted as a sanitary napkin, the view corresponding to FIG. 4C.
Figure 7:
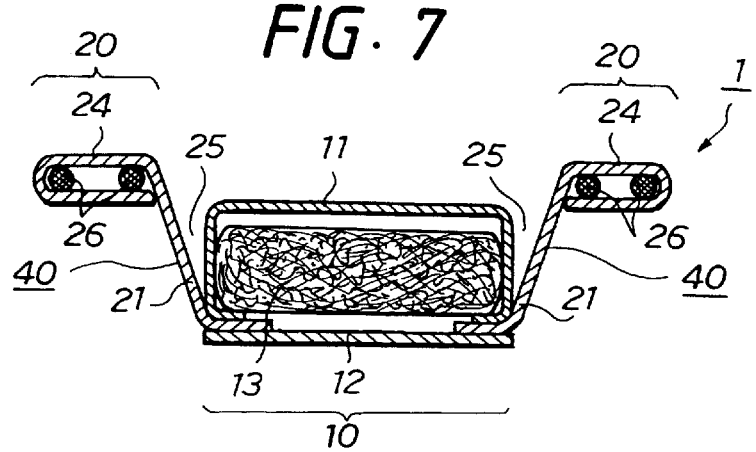
FIG. 7 is a sectional view showing a fourth embodiment of the absorbent article in accordance with the present invention, which is constituted as a sanitary napkin, the view corresponding to FIG. 4C.
Figure 8:
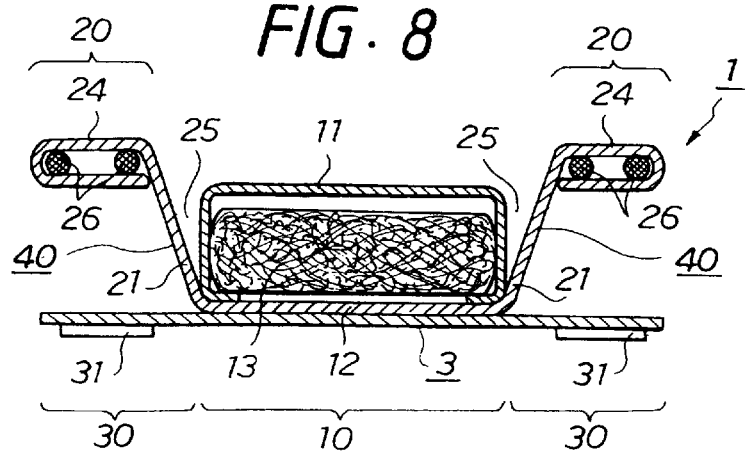
FIG. 8 is a sectional view showing a fifth embodiment of the absorbent article in accordance with the present invention, which is constituted as a sanitary napkin, the view corresponding to FIG. 4C.

FIG. 5 is a sectional view showing the second embodiment of the absorbent article in accordance with the present invention, which is constituted as a sanitary napkin, the view corresponding to FIG. 4C. FIG. 6 is a sectional view showing the third embodiment of the absorbent article in accordance with the present invention, which is constituted as a sanitary napkin, the view corresponding to FIG. 4C. FIG. 7 is a sectional view showing the fourth embodiment of the absorbent article in accordance with the present invention, which is constituted as a sanitary napkin, the view corresponding to FIG. 4C. FIG. 8 is a sectional view showing the fifth embodiment of the absorbent article in accordance with the present invention, which is constituted as a sanitary napkin, the view corresponding to FIG. 4C.

As for the second, third, fourth, and fifth embodiments, only the features different from the first embodiment will be described hereinbelow. As for the features which are not explained in the second through fifth embodiments, the explanation made in the first embodiment is applied. In FIGS. 5 through 8, the same elements as in FIG. 4C are numbered with the same reference numerals.

As illustrated in FIG. 5, in the second embodiment of the sanitary napkin 1, each of the flaps 20, 20 is formed by the topsheet 11. Specifically, the topsheet 11 is joined with the backsheet 12 on the side of the skin-uncontacting surface 3, and each edge of the opposing longitudinal sides of the topsheet 11 is extended outwardly to form the flap 20. In this manner, the flap 20 is connected with the skin-uncontacting surface 3.

As in the flap 20 in the first embodiment described above, the flap 20 forms the antileakage wall 21 and the antileakage surface 24. The flap 20 is folded at the side edge of the antileakage surface 24 toward the skin-uncontacting surface 3. The elastic members 26, 26 are held between the antileakage surface 24 and the folded portion of the flap 20.

In this case, it is necessary for the topsheet 11, which forms the flap 20, to have water-proofness. Examples of the materials for the topsheet 11 capable of being used in this case include a material, which is obtained by carrying out water repellent treatment on the flap-forming portions of an ordinarily used topsheet material, a plastic sheet, in which the absorbent member-contacting portion is porous and the flap-forming portions are not porous, and a nonwoven fabric in which the flap-forming portions have been subjected to a laminating process.

As illustrated in FIG. 6, in the third embodiment of the sanitary napkin 1, each of the flaps 20, 20 is formed by the backsheet 12. Specifically, the backsheet 12 is joined with the topsheet 11 on the side of the skin-uncontacting surface 3, and each edge of the opposing longitudinal sides of the backsheet 12 is extended outwardly to form the flap 20. In this manner, the flap 20 is connected with the skin-uncontacting surface 3.

As in the flap 20 in the first embodiment described above, the flap 20 forms the antileakage wall 21 and the antileakage surface 24. The flap 20 is folded at the side edge of the antileakage surface 24 toward the skin-uncontacting surface 3. The elastic members 26, 26 are held between the antileakage surface 24 and the folded portion of the flap 20.

As illustrated in FIG. 7, in the fourth embodiment of the sanitary napkin 1, the flaps 20, 20 are formed respectively by sheets 40, 40 other than the topsheet 11 and the backsheet 12.

As each of the other sheets 40, 40, a sheet having been subjected to waterproof treatment, a liquid impermeable sheet, or the like, may be employed.

As an example of the sheet having been subjected to waterproof treatment, a nonwoven fabric treated with a water repellent oil agent, or the like, may be mentioned. As examples of the liquid impermeable sheet, a plastic sheet, such as a polyethylene sheet or a polypropylene sheet, a sheet obtained by carrying out a laminating process on a nonwoven fabric, and the like, may be mentioned.

Specifically, the topsheet 11 covers the opposing longitudinal side surfaces of the absorbent member 13 up to the edges of the opposing longitudinal sides at the skin-uncontacting surface 3. At the skin-uncontacting surface 3, the edge portion of the other sheet 40 is held and secured between the topsheet 11 and the backsheet 12. In this manner, the flap 20 is connected with the skin-uncontacting surface 3.

As in the flap 20 in the first embodiment described above, the flap 20 forms the antileakage wall 21 and the antileakage surface 24. The flap 20 is folded at the side edge of the antileakage surface 24 toward the skin-uncontacting surface 3. The elastic members 26, 26 are held between the antileakage surface 24 and the folded portion of the flap 20.

As illustrated in FIG. 8, in the fifth embodiment of the sanitary napkin 1, the flaps 20, 20 are formed by a single sheet 40 other than the topsheet 11 and the backsheet 12. Also, wing portions 30, 30, which have adhesive portions 31, 31 for adhering to the underwear when the sanitary napkin 1 is used, are provided at the skin-uncontacting surface 3.

Specifically, the topsheet 11 covers the opposing longitudinal side surfaces of the absorbent member 13 up to the edges of the opposing longitudinal sides at the skin-uncontacting surface 3. At the skin-uncontacting surface 3, the other sheet 40 is held and secured between the topsheet 11 and the backsheet 12. In this manner, the flap 20 is connected with the skin-uncontacting surface 3.

As in the flap 20 in the first embodiment described above, the flap 20 forms the antileakage wall 21 and the antileakage surface 24. The flap 20 is folded at the side edge of the antileakage surface 24 toward the skin-uncontacting surface 3. The elastic members 26, 26 are held between the antileakage surface 24 and the folded portion of the flap 20.

Also, each of the wing portions 30, 30 is formed by each of extended portions of the opposing lateral side edges of the backsheet 12, which portion is extended outwardly from each edge of the opposing longitudinal sides of the absorbent member 13. Each of the adhesive portions 31, 31 is formed by applying an adhesive agent to the surface of each of the wing portions 30, 30 at the skin-uncontacting surface 3. As the adhesive agent, any of known adhesive agents may be employed. The surface of the portion of the backsheet 12, which portion is adhered to the central absorbent body 10, (i.e., the non-adhered surface) has been subjected to peal treatment. Therefore, before the sanitary napkin 1 is used (i.e., when it is being stored), the wing portion 30 can be folded toward the skin-uncontacting surface 3 and releasably adhered to the surface of the backsheet 12 in order to protect the adhesive portion 31.

With the second, third, fourth, and fifth embodiments described above, the same effects as those with the first embodiment described above can be obtained.

The sixth embodiment of the absorbent article in accordance with the present invention will be described hereinbelow with reference to FIGS. 9, 10A, and 10E.

Figure 9:
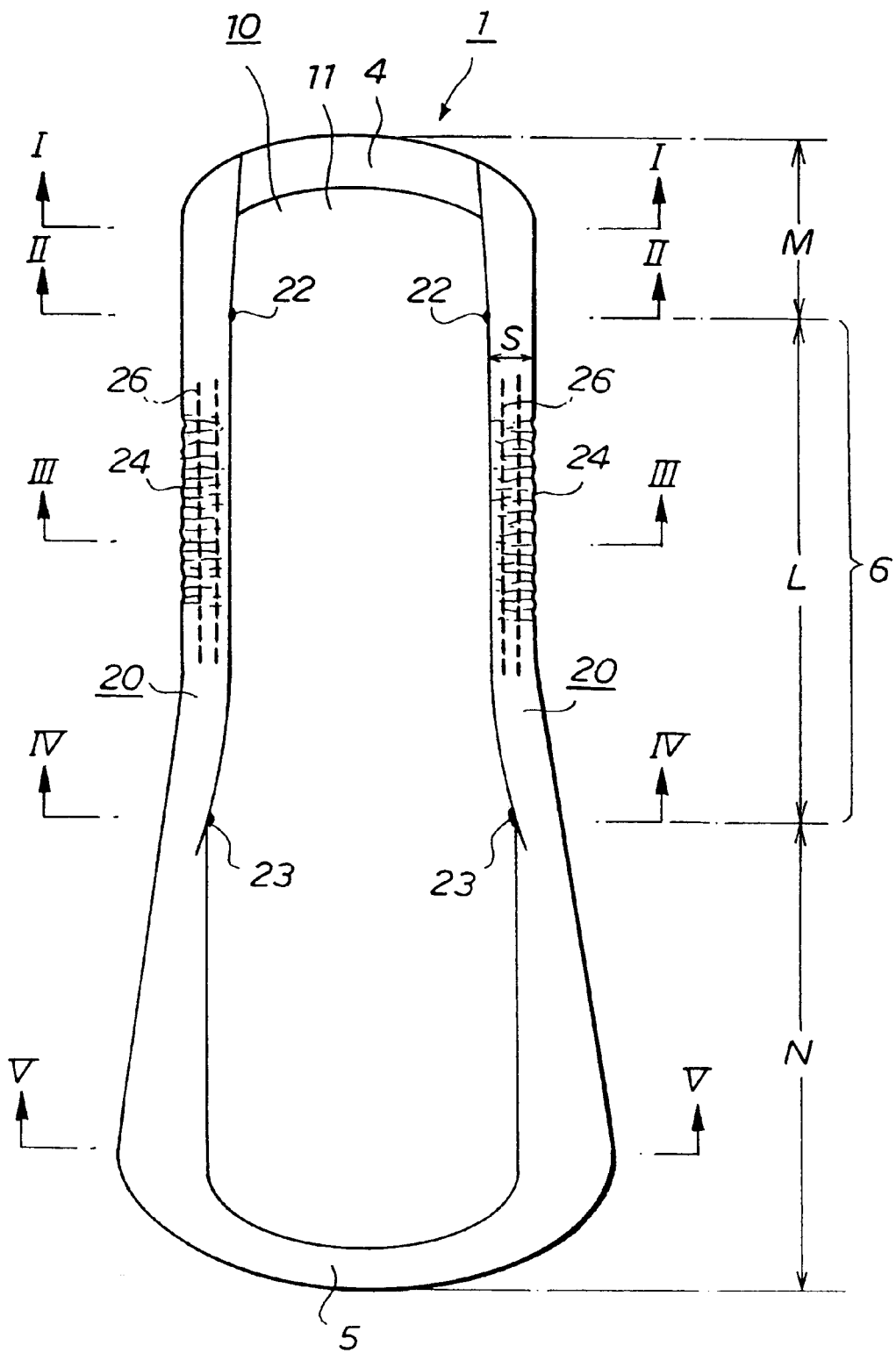
FIG. 9 is a plan view showing a sixth embodiment of the absorbent article in accordance with the present invention, which is constituted as a sanitary napkin.

FIG. 9 is a plan view showing the sixth embodiment of the absorbent article in accordance with the present invention, which is constituted as a sanitary napkin. FIG. 10A is a schematic sectional view taken along line I—I of FIG. 9. FIG. 10E is a schematic sectional view taken along line V—V of FIG. 9.

As for the sixth embodiment, only the features different from the first embodiment will be described hereinbelow. As for the features which are not explained in the sixth embodiment, the explanation made in the first embodiment is applied. The sectional views taken along line II—II, line III—III, and line IV—IV of FIG. 9 are respectively the same as FIGS. 4B, 4C, and 4D. In FIGS. 9, 10A, and 10B, the same elements as in FIG. 1 are numbered with the same reference numerals.

Figure 10A:
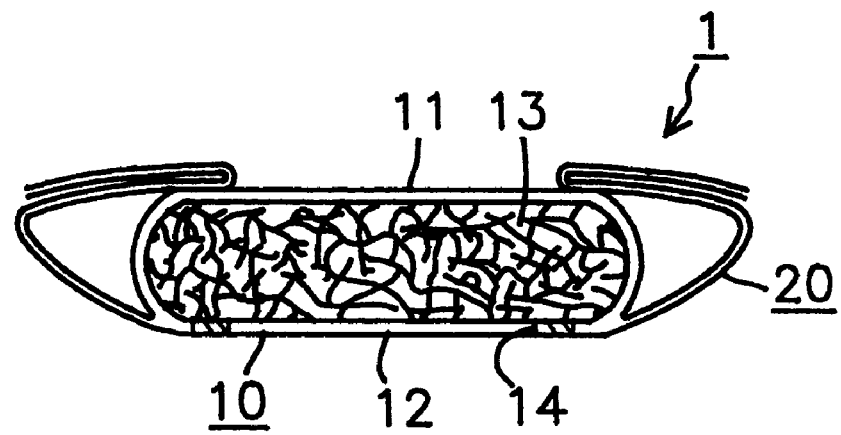
FIG. 10A is a schematic sectional view taken along line I—I of FIG. 9.
Figure 10B:
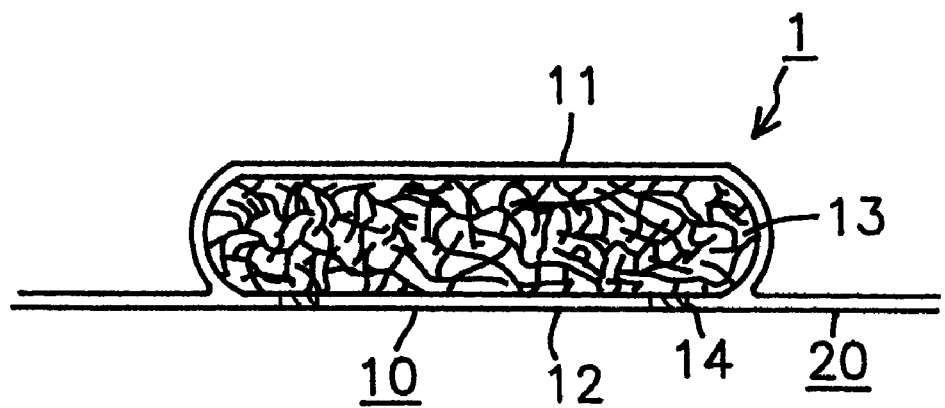
FIG. 10B is a schematic sectional view taken along line V—V of FIG. 9.

As illustrated in FIGS. 9 and 10A, in the sixth embodiment of the sanitary napkin 1, in the front edge portion 4 of the sanitary napkin 1, the folded flap 20 is kept in the folded condition, is heat sealed in this condition with the antileakage surface 24 facing up, and is thus secured. Also, as illustrated in FIGS. 9 and 10E, in the rear edge portion 5, the flap 20 has a substantially flat surface-like shape. Specifically, this embodiment of the sanitary napkin 1 is constituted in such a manner that, in the portion forward from the fixing portions 22, 22 in the front portion (i.e., in the portion which is located on the front side of the wearer when the sanitary napkin is used), the side pocket is formed over the entire area of the portion, in which the central absorbent body 10 and the flap 20 contact with each other. Also, this embodiment of the sanitary napkin 1 is constituted in such a manner that, in the portion rearward from the fixing portions 23, 23 in the rear portion (i.e., in the portion which is located on the rear side of the wearer when the sanitary napkin is used), the aforesaid folded condition of the flap 20 is released gradually toward the rear side in such a manner that the flap 20 takes a substantially flat surface-like shape.

The sixth embodiment of the sanitary napkin 1 has the structure described above. Therefore, in particular, leakage on both sides and rear leakage can be prevented effectively. Accordingly, this embodiment is suitable particularly for night use and for long-time use.

A seventh embodiment of the absorbent article in accordance with the present invention will be described hereinbelow with reference to FIGS. 11 and 12.

Figure 11:
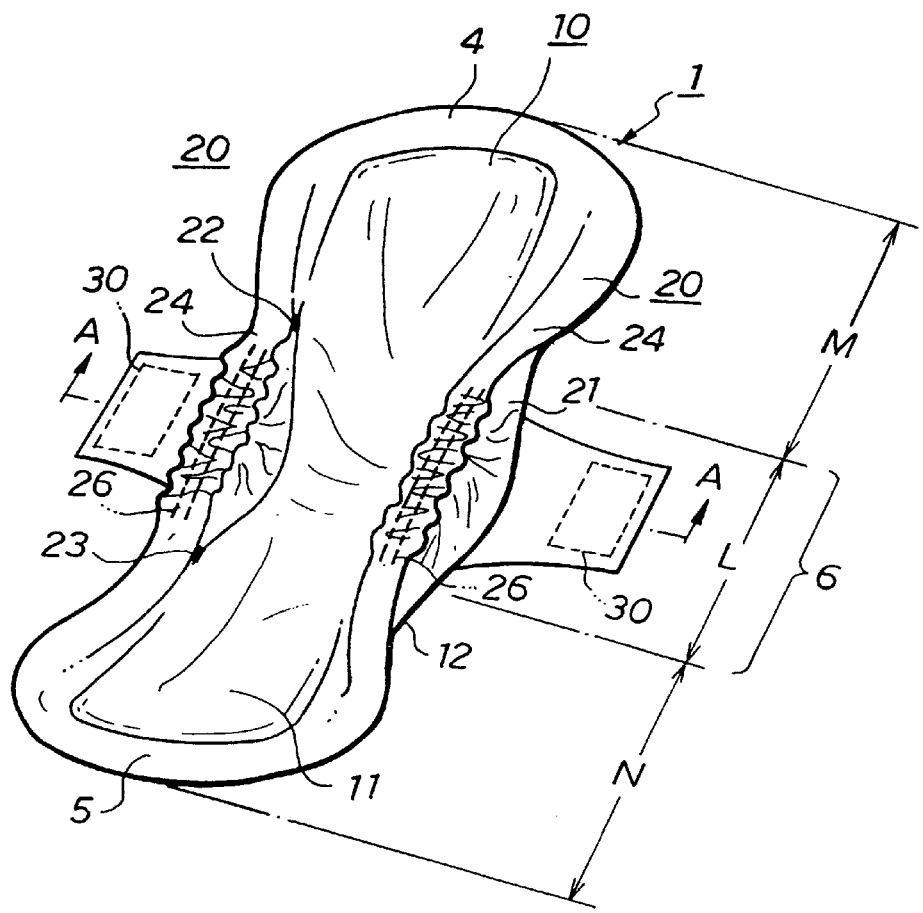
FIG. 11 is a perspective view showing a seventh embodiment of the absorbent article in accordance with the present invention, which is constituted as a sanitary napkin.

FIG. 11 is a perspective view showing the seventh embodiment of the absorbent article in accordance with the present invention, which is constituted as a sanitary napkin. FIG. 12 is a schematic sectional view taken along line A—A of FIG. 11.

As for the seventh embodiment, only the features different from the first embodiment will be described hereinbelow. As for the features which are not explained in the seventh embodiment, the explanation made in the first embodiment is applied. In FIGS. 11 and 12, the same elements as in FIG. 1 are numbered with the same reference numerals.

In the seventh embodiment of the sanitary napkin 1, wing portions for fixing the absorbent article in use are provided in such a manner that the wing portions are connected with the surface of the absorbent article, which does not contact the skin of the wearer, in the opposing longitudinal sides of the central absorbent body of the aforesaid first embodiment of the sanitary napkin 1.

Specifically, wing portions 30, 30 are formed by adhering a rectangular sheet 32 to the surface of the backsheet 12 and by thus being connected with the opposing longitudinal sides of the central absorbent body 10. Each of the wing portions 30, 30 is provided with an adhesive portion 31 at the skin-uncontacting surface 3.

As the rectangular sheet 32, it is possible to employ a plastic sheet, such as a polyethylene sheet or a polyethylene terephthalate (PET) sheet, or paper or nonwoven fabric having been subjected to a laminating process. Each of the adhesive portions 31, 31 is formed by applying an adhesive agent to the surface of each of the wing portions 30, 30 at the skin-uncontacting surface 3. As the adhesive agent, any of known adhesive agents may be employed.

With the wing portions 30, 30, the sanitary napkin 1 can be secured more firmly to the underwear.

Eighth through twelfth embodiments of the absorbent article in accordance with the present invention will be described hereinbelow with reference to FIGS. 13 through 17B.

Figure 12:
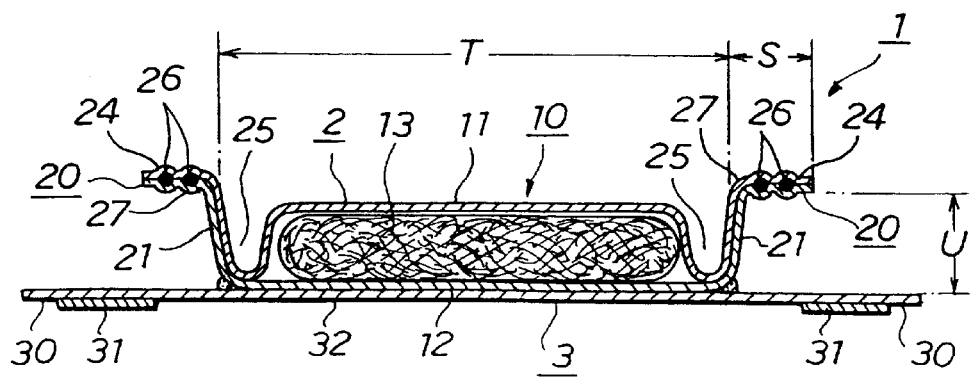
FIG. 12 is a schematic sectional view taken along line A—A of FIG. 11.
Figure 13:
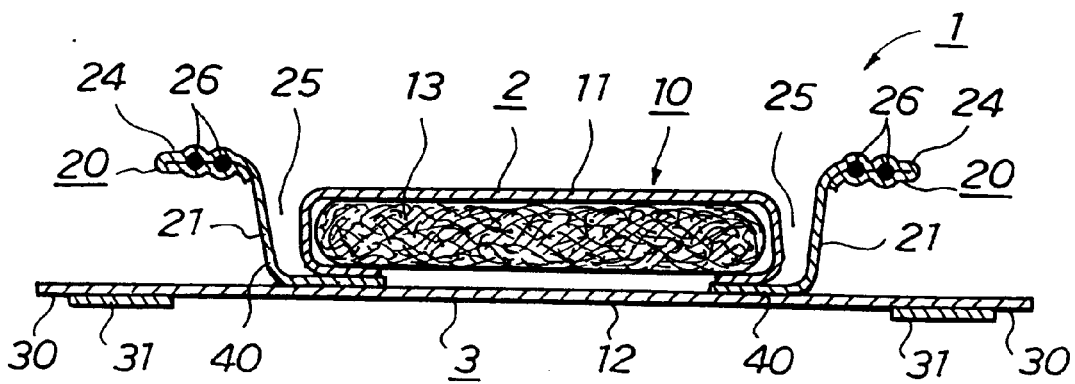
FIG. 13 is a sectional view showing an eighth embodiment of the absorbent article in accordance with the present invention, which is constituted as a sanitary napkin, the view corresponding to FIG. 12.
Figure 14:
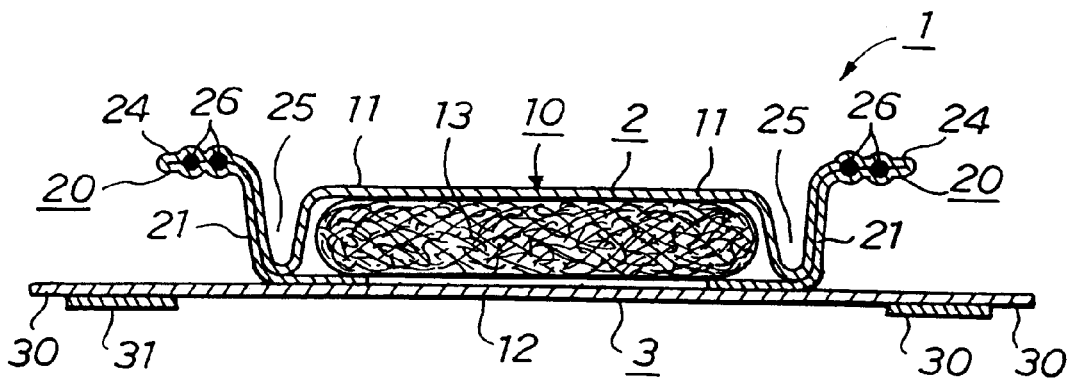
FIG. 14 is a sectional view showing a ninth embodiment of the absorbent article in accordance with the present invention, which is constituted as a sanitary napkin, the view corresponding to FIG. 12.
Figure 15:
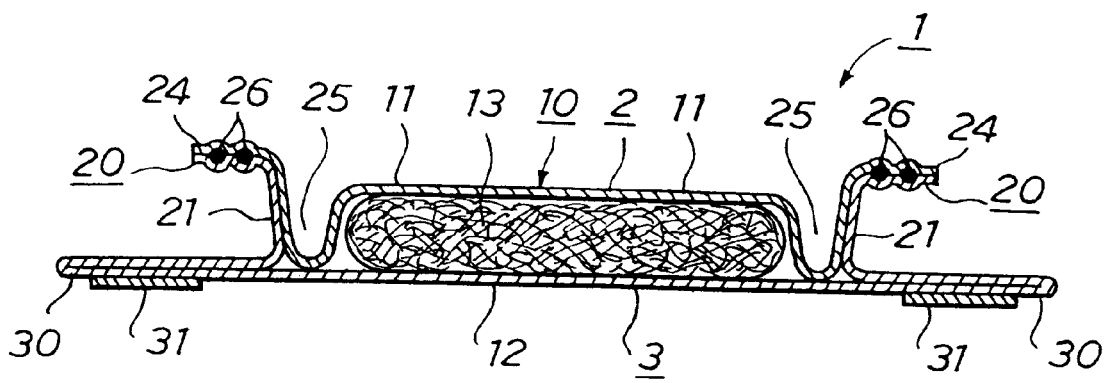
FIG. 15 is a sectional view showing a tenth embodiment of the absorbent article in accordance with the present invention, which is constituted as a sanitary napkin, the view corresponding to FIG. 12.
Figure 16:
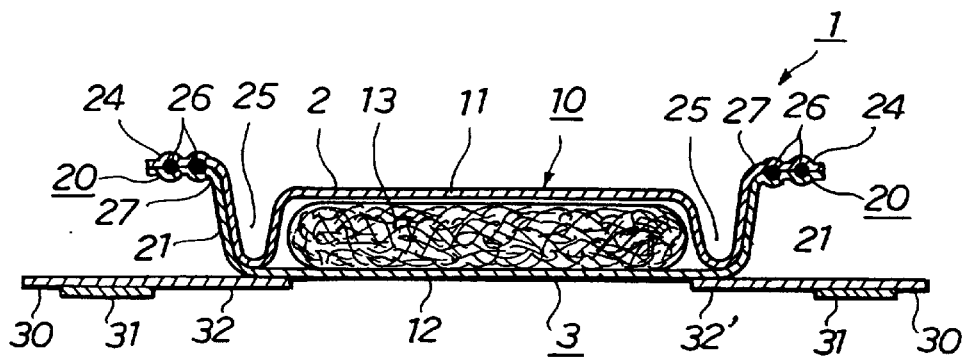
FIG. 16 is a sectional view showing an eleventh embodiment of the absorbent article in accordance with the present invention, which is constituted as a sanitary napkin, the view corresponding to FIG. 12.
Figure 17A:
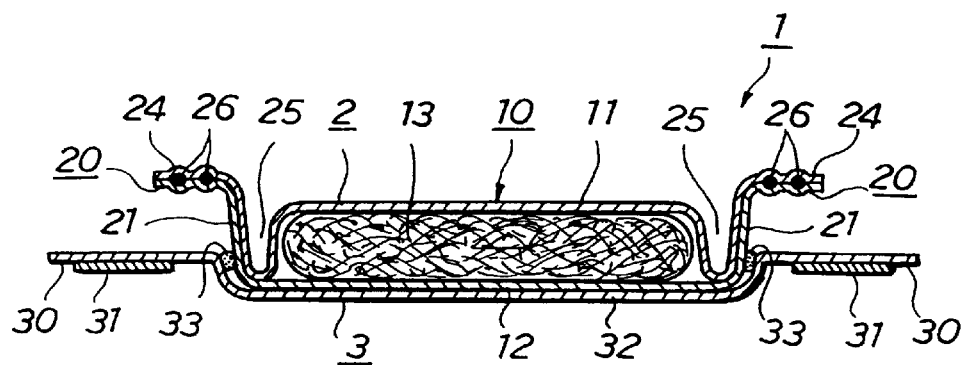
FIG. 17A is a sectional view showing a twelfth embodiment of the absorbent article in accordance with the present invention, which is constituted as a sanitary napkin, the view corresponding to FIG. 12.
Figure 17B:
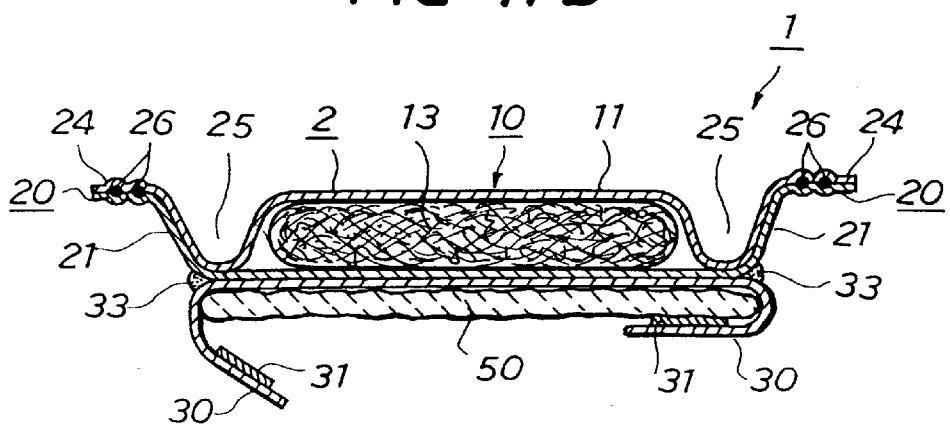
FIG. 17B is a sectional view showing the sanitary napkin of FIG. 17A fitted to shorts.

FIG. 13 is a sectional view showing the eighth embodiment of the absorbent article in accordance with the present invention, which is constituted as a sanitary napkin, the view corresponding to FIG. 12. FIG. 14 is a sectional view showing the ninth embodiment of the absorbent article in accordance with the present invention, which is constituted as a sanitary napkin, the view corresponding to FIG. 12. FIG. 15 is a sectional view showing the tenth embodiment of the absorbent article in accordance with the present invention, which is constituted as a sanitary napkin, the view corresponding to FIG. 12. FIG. 16 is a sectional view showing the eleventh embodiment of the absorbent article in accordance with the present invention, which is constituted as a sanitary napkin, the view corresponding to FIG. 12. FIG. 17A is a sectional view showing the twelfth embodiment of the absorbent article in accordance with the present invention, which is constituted as a sanitary napkin, the view corresponding to FIG. 12. FIG. 17B is a sectional view showing the sanitary napkin of FIG. 17A fitted to shorts.

As for the eighth through twelfth embodiments, only the features different from the aforesaid seventh embodiment will be described hereinbelow. As for the features which are not explained in the eighth through twelfth embodiments, the explanation made in the first and seventh embodiments is applied. In FIGS. 13 through 17B, the same elements as in FIG. 12 are numbered with the same reference numerals.

As illustrated in FIG. 13, in the eighth embodiment of the sanitary napkin 1, the flaps 20, 20 are formed by sheets 40, 40 other than the topsheet 11 and the backsheet 12. Also, each of the wing portions 30, 30 is formed by each of extended portions of the opposing lateral side edges of the backsheet 12, which portion is extended outwardly from each edge of the opposing longitudinal sides of the absorbent member 13. The extended portions correspond to the contacting portion 6.

As for the other sheets 40, 40, the explanation described for the aforesaid fourth embodiment is applied.

Specifically, in the eighth embodiment of the sanitary napkin 1, the topsheet 11 covers the opposing longitudinal side surfaces of the absorbent member 13 up to the edges of the opposing longitudinal sides at the skin-uncontacting surface 3. At the skin-uncontacting surface 3, each of the other sheets 40, 40 is held and secured between the topsheet 11 and the backsheet 12. In this manner, the flap 20 is connected with the skin-uncontacting surface 3.

As in the flap 20 in the seventh embodiment described above, the flap 20 forms the antileakage wall 21 and the antileakage surface 24. The flap 20 is folded at the side edge of the antileakage surface 24 toward the skin-uncontacting surface 3. The elastic members 26, 26 are held between the antileakage surface 24 and the folded portion of the flap 20.

As illustrated in FIG. 14, in the ninth embodiment of the sanitary napkin 1, the flaps 20, 20 are formed by the topsheet 11. Also, each of the wing portions 30, 30 is formed by each of extended portions of the opposing lateral side edges of the backsheet 12, which portion is extended outwardly from each edge of the opposing longitudinal sides of the absorbent member 13. The extended portions correspond to the contacting portion 6.

Specifically, the topsheet 11 covers the opposing longitudinal side surfaces of the absorbent member 13, and each of the opposing longitudinal side edges of the topsheet 11 is extended outwardly. In this manner, the flap 20 is connected with the skin-uncontacting surface 3. Also, at the skin-uncontacting surface 3 of the absorbent member 13, the end portions of the topsheet 11 are held and secured between the absorbent member 13 and the backsheet 12.

As in the flap 20 in the seventh embodiment described above, the flap 20 forms the antileakage wall 21 and the antileakage surface 24. The flap 20 is folded at the side edge of the antileakage surface 24 toward the skin-uncontacting surface 3. The elastic members 26, 26 are held between the antileakage surface 24 and the folded portion of the flap 20.

In this case, it is necessary for the topsheet 11, which forms the flap 20, to have water-proofness. As the material for the topsheet 11 capable of being used in this case, any of various materials described above for the second embodiment may be employed.

As illustrated in FIG. 15, in the tenth embodiment of the sanitary napkin 1, the flaps 20, 20 are formed by the topsheet 11 and the backsheet 12. Also, each of the wing portions 30, 30 is formed by the backsheet 12. Specifically, each of the wing portions 30, 30 is formed by each of extended portions of the opposing lateral side edges of the backsheet 12, which portion is extended outwardly from each edge of the opposing longitudinal sides of the absorbent member 13. The extended portions correspond to the contacting portion 6. Further, the backsheet 12 is then folded toward the topsheet 11 and sealed with the topsheet 11 to form each of the flaps 20, 20 as in the aforesaid seventh embodiment. Each of the flaps 20, 20 forms the antileakage wall 21 and the antileakage surface 24.

In this sanitary napkin 1, the entire flap 20 is formed by the backsheet 12 and the topsheet 11. The flap 20 and the wing portion 30 can be formed by extending the backsheet 12 over its entire longitudinal side, folding the backsheet 12, sealing the backsheet 12 with the topsheet 11 to form the flap 20 over the entire side of the central absorbent body 10, thereafter folding the backsheet 12, and cutting the two-ply folded portions in accordance with the desired shape of the wing portion 30 to form the wing portion 30.

As illustrated in FIG. 16, in the eleventh embodiment of the sanitary napkin 1, each of the wing portions 30, 30 is formed by each of two sheets 32, 32', which are overlaid upon the opposing longitudinal sides of the skin-uncontacting surface 3. The other features are the same as those of the seventh embodiment described above.

As illustrated in FIG. 17A, in the twelfth embodiment of the sanitary napkin 1, each of the wing portions 30, 30 is secured to the corresponding flap 20 at a position slightly upper than the level of the skin-uncontacting surface 3 by each of adhering portions 33, 33, which are formed by applying an adhesive agent along the longitudinal direction of the central absorbent body 10. The other features are the same as those of the seventh embodiment described above.

The position slightly upper than the level of the skin-uncontacting surface 3 should preferably be such that the position is upper than the level of the skin-uncontacting surface 3 and lower than the level of the antileakage surface 24, and such that the antileakage surface 24 does not become lower than the level of the skin-contacting surface 2 when the sanitary napkin 1 is fitted to shorts in use and the side pocket 25 is formed.

Since the twelfth embodiment of the sanitary napkin 1 is constructed in the manner described above, when the sanitary napkin 1 in use is fitted to shorts 50 as shown in FIG. 17B, larger side pockets 25, 25 can be formed. Therefore, leakage on both sides can be prevented more effectively.

With the eighth through twelfth embodiments described above, the same effects as those with the aforesaid seventh embodiment can be obtained.

A thirteenth embodiment of the absorbent article in accordance with the present invention will be described hereinbelow with reference to FIGS. 19, 20, and 21.

Figure 19:
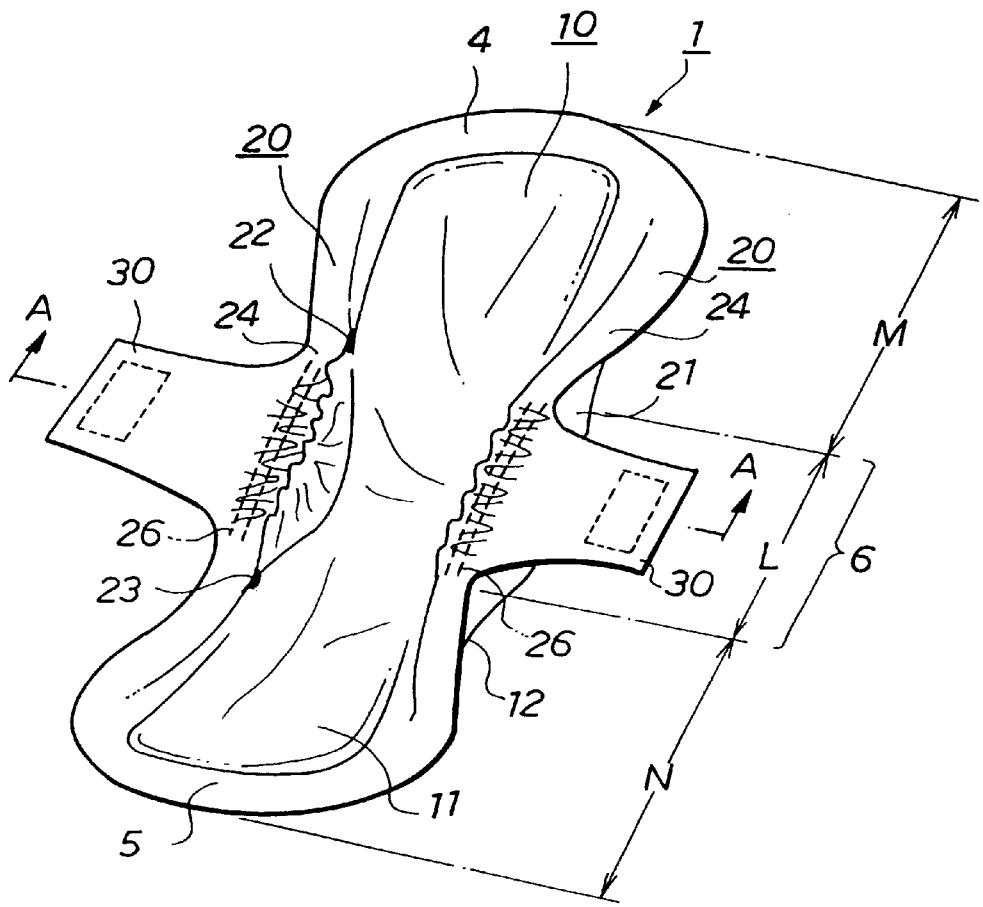
FIG. 19 is a perspective view showing a thirteenth embodiment of the absorbent article in accordance with the present invention, which is constituted as a sanitary napkin.

FIG. 19 is a perspective view showing the thirteenth embodiment of the absorbent article in accordance with the present invention, which is constituted as a sanitary napkin. FIG. 20 is a schematic sectional view taken along line A—A of FIG. 19. FIG. 21 is a sectional view showing the sanitary napkin of FIG. 19 fitted to shorts.

As for the thirteenth embodiment, only the features different from the first embodiment will be described hereinbelow. As for the features which are not explained in the thirteenth embodiment, the explanation made in the first embodiment is applied. In FIGS. 19, 20, and 21, the same elements as in FIG. 1 are numbered with the same reference numerals.

In the thirteenth embodiment of the sanitary napkin 1, each of the wing portions for fixing the absorbent article in use is formed by extending the antileakage surface in the aforesaid first embodiment of the sanitary napkin 1.

Specifically, each of the wing portions 30, 30 is formed by each of extended portions of the opposing lateral side edges of the topsheet 11 and the backsheet 12 at the antileakage surfaces 24, 24, which portion is extended outwardly from each edge of the opposing longitudinal sides of the absorbent member 13. Each of the wing portions 30, 30 is provided with the adhesive portion 31 on the side facing the skin-uncontacting surface 3. The adhesive portion 31 is formed by applying an adhesive agent. As the adhesive agent, any of known adhesive agents may be employed.

In the thirteenth embodiment of the sanitary napkin 1, the length of each wing portion 30, as measured along the width direction of the sanitary napkin 1, should preferably fall within the range of 10 to 100 mm, and should more preferably fall within the range of 20 to 80 mm.

Since the thirteenth embodiment of the sanitary napkin 1 is provided with the wing portions 30, 30, the antileakage wall 21 and the antileakage surface 24 can be formed in a stable manner.

Figure 21:
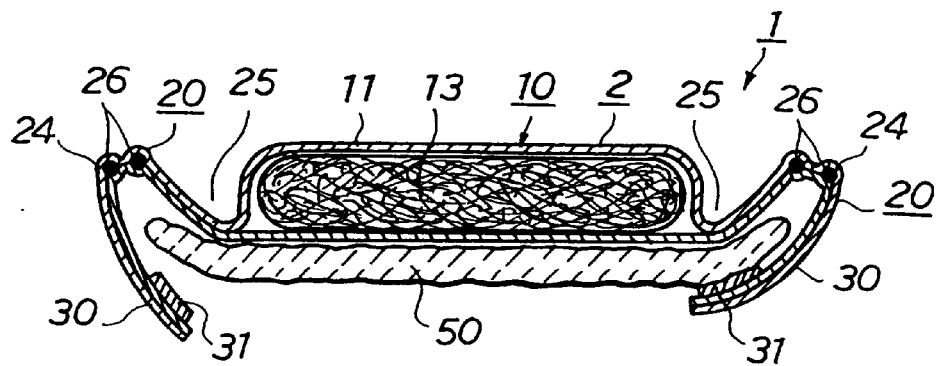
FIG. 21 is a sectional view showing the sanitary napkin of FIG. 19 fitted to shorts.

As illustrated in FIG. 21, when the sanitary napkin 1 is used, the wing portions 30, 30 are folded toward the shorts 50, and the adhesive portions 31, 31 are adhered to the surface of the shorts 50. In this manner, the sanitary napkin 1 can be secured firmly and can be prevented from slipping off during the use. Also, with this embodiment of the sanitary napkin 1 having the structure described above, when it is used, the side pockets 25, 25 larger than those in a sanitary napkin having no wing portion 30 can be formed, and leakage on both sides can be prevented more effectively.

Fourteenth, fifteenth, and sixteenth embodiments of the absorbent article in accordance with the present invention will be described hereinbelow with reference to FIGS. 22, 23, and 24.

Figure 20:
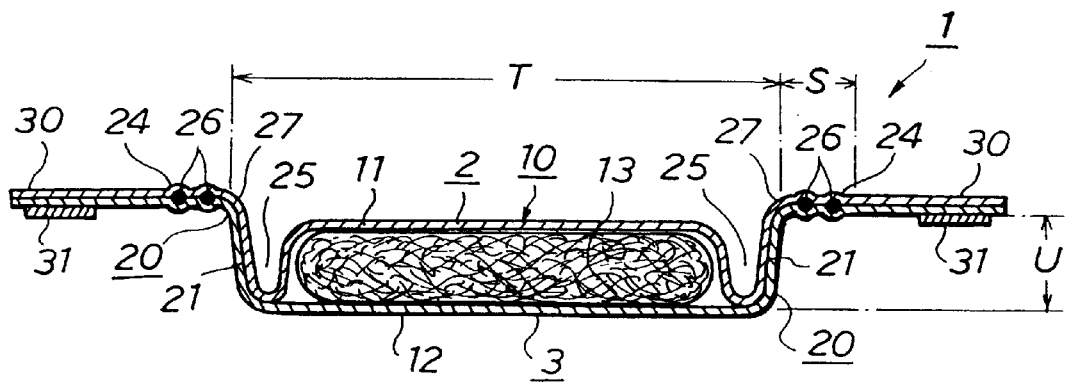
FIG. 20 is a schematic sectional view taken along line A—A of FIG. 19.
Figure 22:
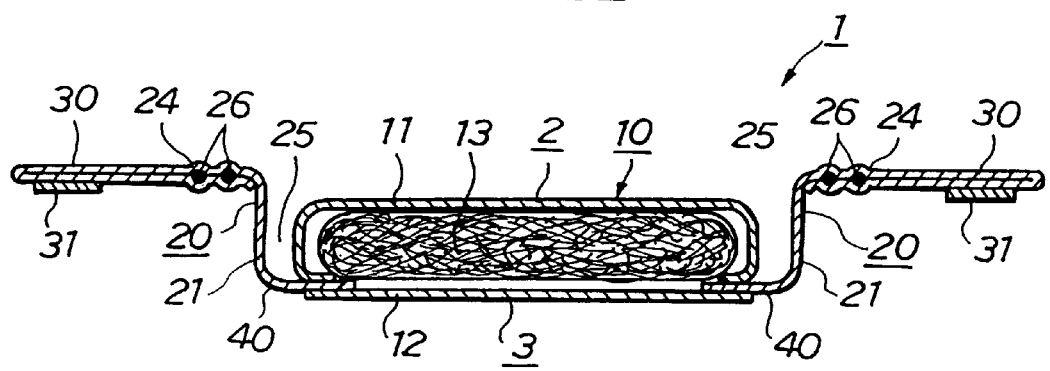
FIG. 22 is a sectional view showing a fourteenth embodiment of the absorbent article in accordance with the present invention, which is constituted as a sanitary napkin, the view corresponding to FIG. 20.

FIG. 22 is a sectional view showing the fourteenth embodiment of the absorbent article in accordance with the present invention, which is constituted as a sanitary napkin, the view corresponding to FIG. 20. FIG. 23 is a sectional view showing the fifteenth embodiment of the absorbent article in accordance with the present invention, which is constituted as a sanitary napkin, the view corresponding to FIG. 20. FIG. 24 is a perspective view showing the sixteenth embodiment of the absorbent article in accordance with the present invention, which is constituted as a sanitary napkin, the view corresponding to FIG. 19.

As for the fourteenth, fifteenth, and sixteenth embodiments, only the features different from the aforesaid thirteenth embodiment will be described hereinbelow. As for the features which are not explained in the fourteenth, fifteenth, and sixteenth embodiments, the explanation made in the first and thirteenth embodiments is applied. In FIGS. 22, 23, and 24, the same elements as in FIGS. 19 and 20 are numbered with the same reference numerals.

As illustrated in FIG. 22, in the fourteenth embodiment of the sanitary napkin 1, the flaps 20, 20 are formed by sheets 40, 40 other than the topsheet 11 and the backsheet 12.

As for the other sheets 40, 40, the explanation described for the aforesaid fourth embodiment is applied.

Specifically, in the fourteenth embodiment of the sanitary napkin 1, the topsheet 11 covers the opposing longitudinal side surfaces of the absorbent member 13 up to the edges of the opposing longitudinal sides at the skin-uncontacting surface 3. At the skin-uncontacting surface 3, each of the other sheets 40, 40 is held and secured between the topsheet 11 and the backsheet 12. In this manner, the flap 20 is connected with the skin-uncontacting surface 3.

As in the flap 20 in the thirteenth embodiment described above, the flap 20 forms the antileakage wall 21, the antileakage surface 24, and the wing portion 30. The flap 20 is folded at the side edge of the antileakage surface 24 and the side edge of the wing portion 30 toward the skin-uncontacting surface 3. The elastic members 26, 26 are held between the antileakage surface 24 and the folded portion of the flap 20.

Figure 23:
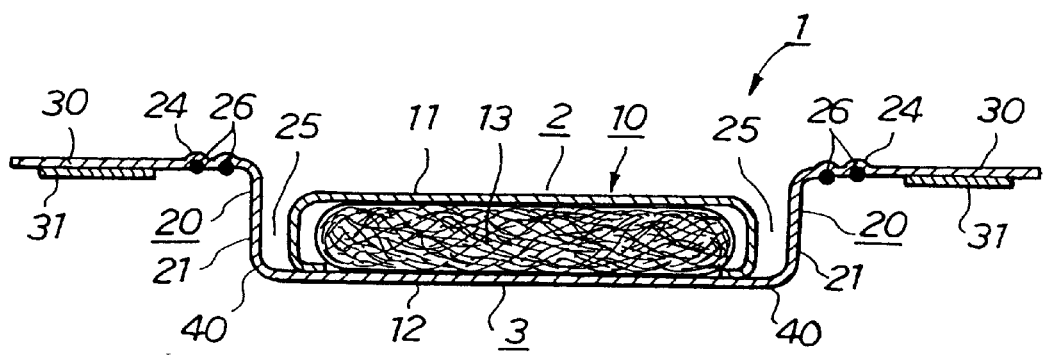
FIG. 23 is a sectional view showing a fifteenth embodiment of the absorbent article in accordance with the present invention, which is constituted as a sanitary napkin, the view corresponding to FIG. 20.

As illustrated in FIG. 23, in the fifteenth embodiment of the sanitary napkin 1, each of the flaps 20, 20 and each of the wing portions 30, 30 are formed by the backsheet 12. Specifically, the backsheet 12 is joined with the topsheet 11 on the side of the skin-uncontacting surface 3, and each edge of the opposing longitudinal sides of the backsheet 12 is extended outwardly to form the flap 20. In this manner, the flap 20 is connected with the skin-uncontacting surface 3.

Further, in the contacting portion 6, the flap 20 is extended outwardly to form the wing portion 30.

The elastic members 26, 26 are secured to the flap 20 at the antileakage surface 24 by an adhesive agent or by being covered with a thermoplastic resin, or the like, and subjected to heat treatment.

Figure 24:
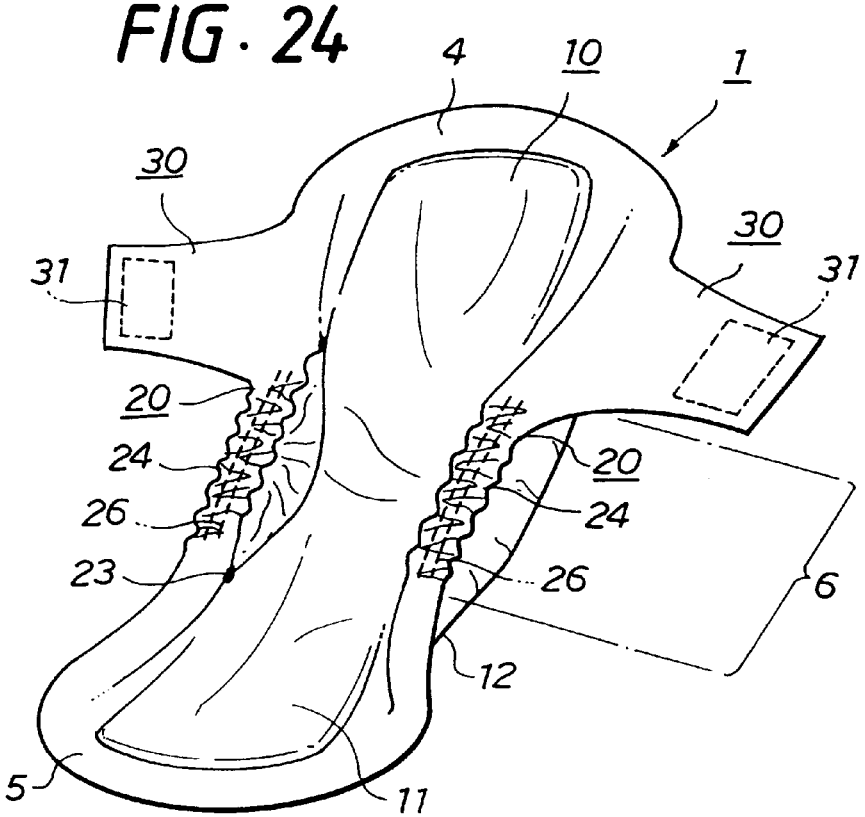
FIG. 24 is a perspective view showing a sixteenth embodiment of the absorbent article in accordance with the present invention, which is constituted as a sanitary napkin, the view corresponding to FIG. 19.
Figure 25:
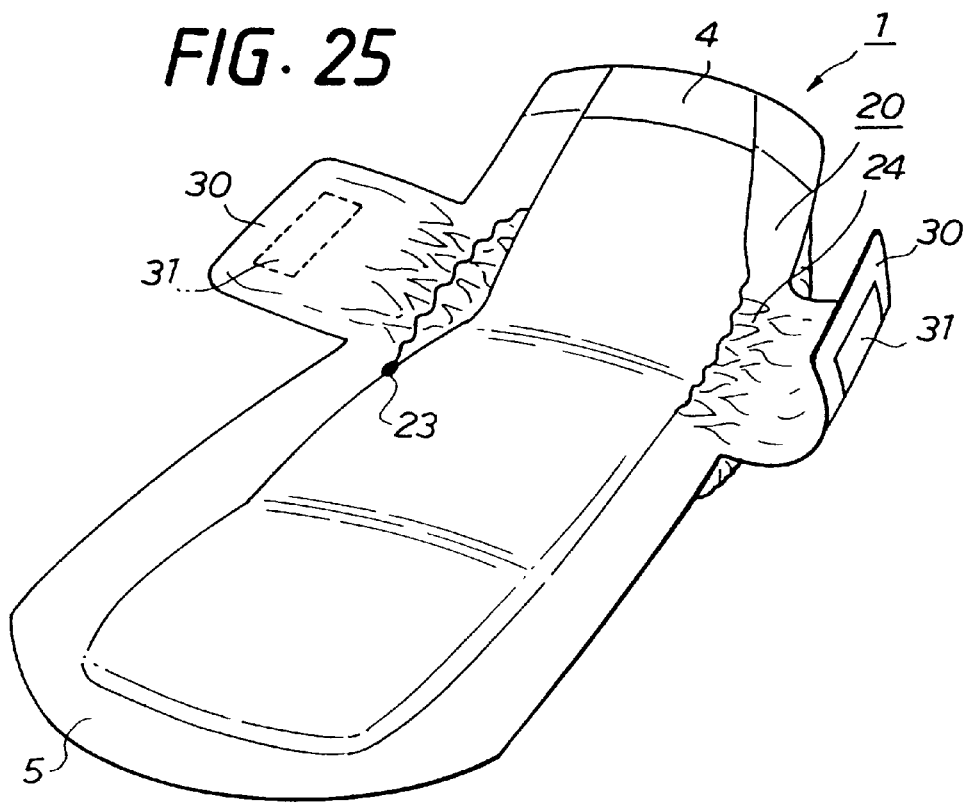
FIG. 25 is a perspective view showing another embodiment of the absorbent article in accordance with the present invention, which is constituted as a sanitary napkin.

As illustrated in FIG. 24, in the sixteenth embodiment of the sanitary napkin 1, each of the flaps 20, 20 is extended outwardly in the portion forward from the contacting portion 6, and each of the wing portions 30, 30 is formed in the portion forward from the contacting portion 6.

Thus in the absorbent article in accordance with the present invention, no limitation is imposed on the position, at which each of the wing portions is located.

With the fourteenth, fifteenth, and sixteenth embodiments described above, the same effects as those with the thirteenth embodiment can be obtained.

Seventeenth through twenty-first embodiments of the absorbent article in accordance with the present invention will be described hereinbelow with reference to FIGS. 26 through 33.

Figure 26:
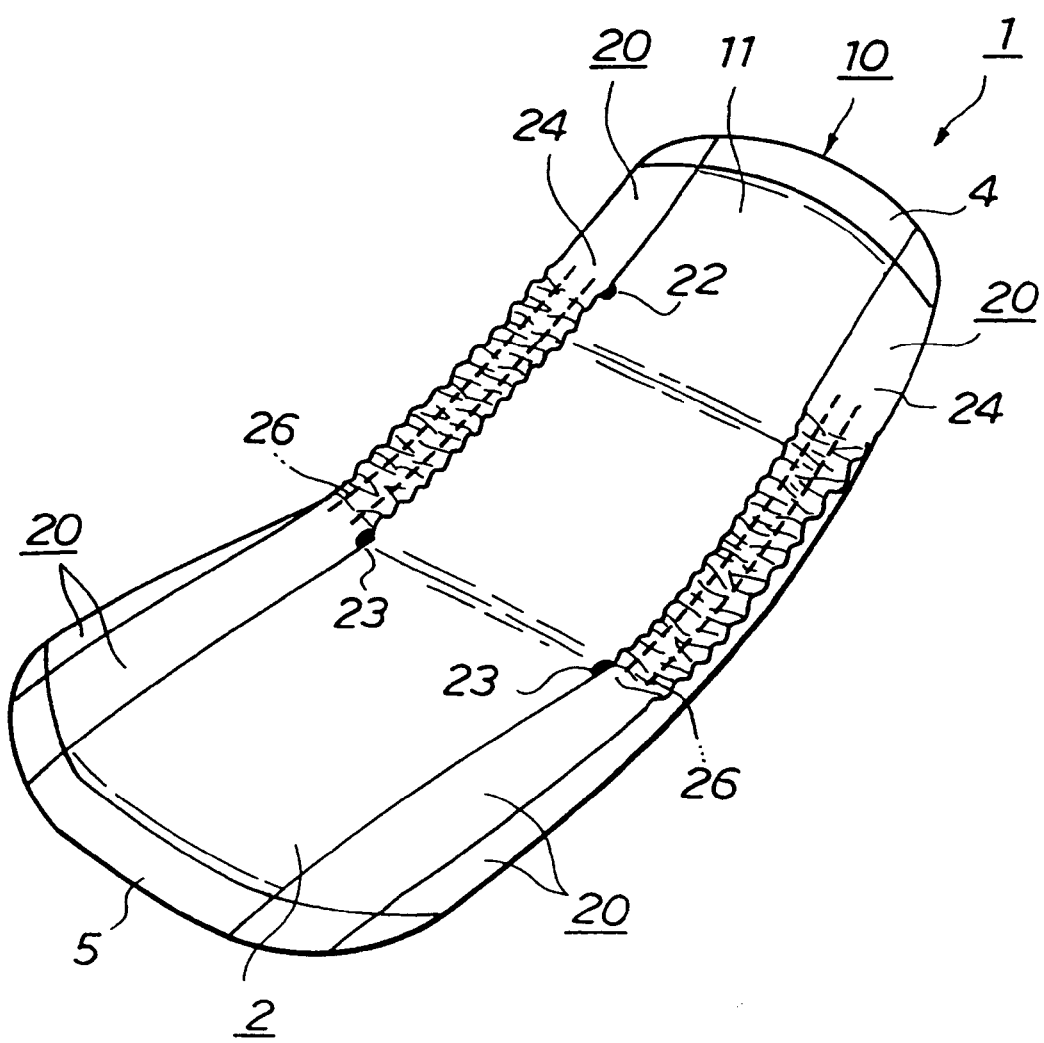
FIG. 26 is a perspective view showing an seventeenth embodiment of the absorbent article in accordance with the present invention, which is constituted as a sanitary napkin.
Figure 27:
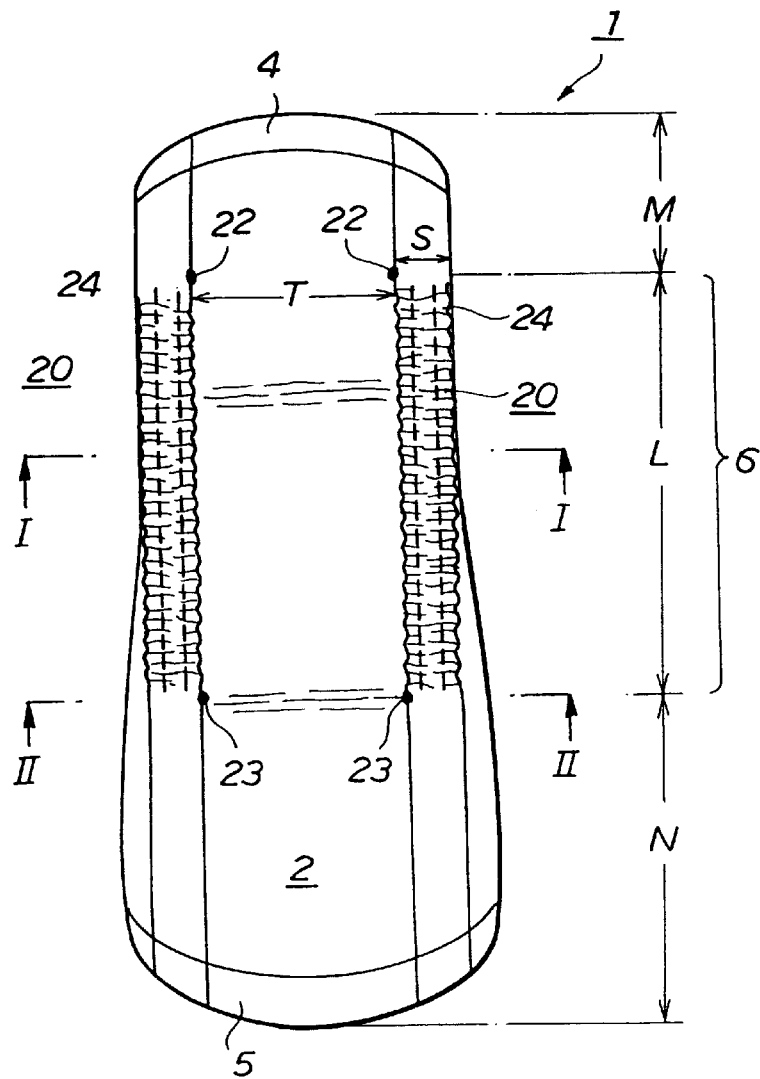
FIG. 27 is a plan view showing the sanitary napkin of FIG. 26.
Figure 28:
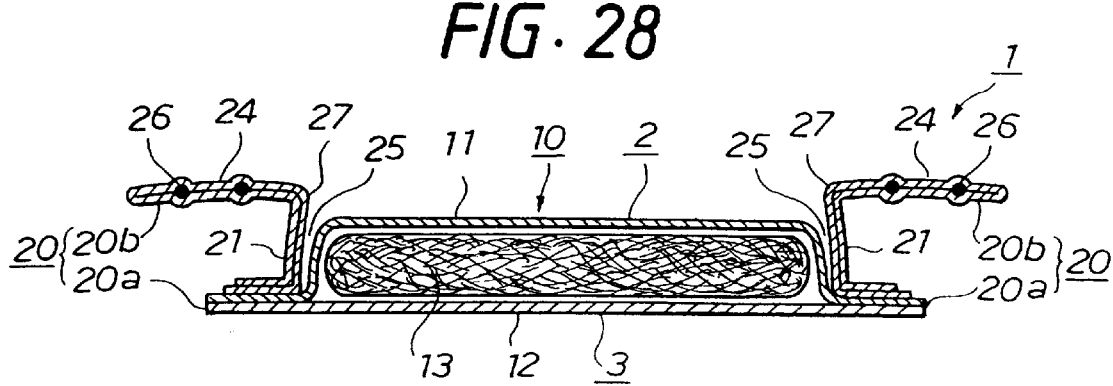
FIG. 28 is a schematic sectional view taken along line I—I of FIG. 27.
Figure 29:
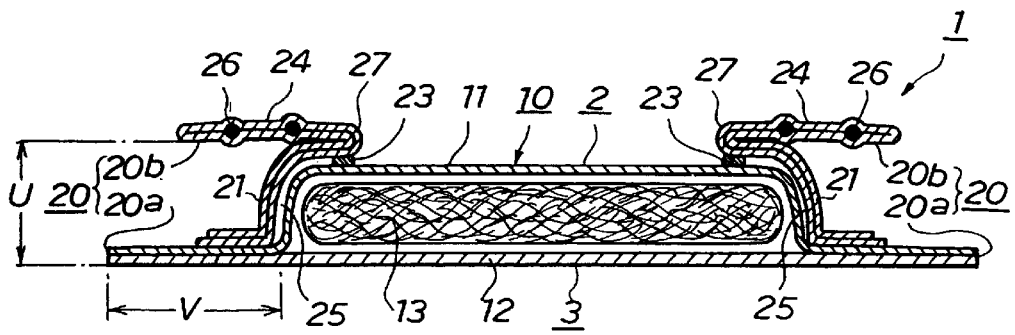
FIG. 29 is a schematic sectional view taken along line II—II of FIG. 27.

FIG. 26 is a perspective view showing the seventeenth embodiment of the absorbent article in accordance with the present invention, which is constituted as a sanitary napkin. FIG. 27 is a plan view showing the sanitary napkin of FIG. 26. FIG. 28 is a schematic sectional view taken along line I—I of FIG. 27. FIG. 29 is a schematic sectional view taken along line II—II of FIG. 27.

As for the seventeenth embodiment, only the features different from the aforesaid first embodiment will be described hereinbelow. As for the features which are not explained in the seventeenth embodiment, the explanation made for the aforesaid first embodiment is applied. In FIGS. 26, 27, 28 and 29, the same elements as in FIGS. 1, 3, and 4A through 4D are numbered with the same reference numerals.

The seventeenth embodiment of the sanitary napkin has a central absorbent body comprising a liquid permeable topsheet, a liquid impermeable backsheet and an absorbent member interposed between the topsheet and the backsheet. Also, the sanitary napkin has a pair of flaps provided in the opposing longitudinal sides of the central absorbent body. Each of the flaps is connected with the surface of the absorbent article which, in use, does not contact the skin of the wearer. Also, each of the flaps forms an antileakage wall along each edge of the opposing longitudinal sides of the central absorbent body. Further, each of the flaps is folded outwardly from the central absorbent body to form an antileakage surface. The antileakage surface in the portion which contacts the discharging portion of the wearer in use is a surface substantially parallel to the surface of the absorbent article which, in use, contacts the skin of the wearer. The flap comprises a first flap and a second flap. The e folded portion of the flap 20.

As illustrated in FIG. 23, in the fifteenth em first flap is formed by at least an extended portion of the backsheet. The second flap is formed by an antileakage sheet. The lower portion of the second flap is secured to the first flap. The antileakage wall and the antileakage surface are formed by the second flap.

Specifically, as illustrated in FIGS. 26 and 27, the seventeenth embodiment of the sanitary napkin 1 has a central absorbent body 10 comprising a liquid permeable topsheet 11, a liquid impermeable backsheet 12 and an absorbent member 13 interposed between the topsheet 11 and the backsheet 12. Also, the sanitary napkin has a pair of flaps 20, 20 provided in the opposing longitudinal sides of the central absorbent body. Such a structure is similar to the structure of an ordinary sanitary napkin.

As illustrated in FIGS. 26, 27, 28, and 29, in the seventeenth embodiment of the sanitary napkin 1, each of the flaps 20, 20 comprises a first flap 20a, which is formed by an extended portion of the topsheet 11 and an extended portion of the backsheet 12, and a second flap 20b formed by the antileakage sheet. The lower portion of the second flap 20b is secured to the first flap 20a. Also, the second flap 20b forms the antileakage wall 21 along each edge of the opposing longitudinal sides of the central absorbent body 10. Further, the second flap 20b is folded outwardly from the central absorbent body 10 to form the antileakage surface 24. The antileakage surface 24 in the contacting portion 6 is a surface substantially parallel to the skin-contacting surface 2.

More specifically, as illustrated in FIGS. 26, 28, and 29, the first flap 20a is formed by extending the topsheet 11 and the backsheet 12 outwardly from each edge of the opposing longitudinal sides of the central absorbent body 10 and adhering the extended portion of the topsheet 11 and the extended portion of the backsheet 12 to each other. The extended portion of the topsheet 11 and the extended portion of the backsheet 12 are adhered to each other by a heat sealing process, by an adhesive agent, or the like.

The lower portion of the second flap 20b is secured by the heat sealing process, or the like, to the side edge of the first flap 20a along the longitudinal direction of the first flap 20a. The second flap 20b is folded upwardly at the side edge of the central absorbent body 10 to form the antileakage wall 21. Further, at a position slightly upper than the level of the skin-contacting surface 2 of the sanitary napkin 1, the second flap 20b is folded outwardly from the central absorbent body 10 to form the antileakage surface 24.

Also, as illustrated in FIGS. 26, 28, and 29, in the seventeenth embodiment of the sanitary napkin 1, in the front edge portion 4 and the rear edge portion 5 of the sanitary napkin 1, the folded flap 20 is kept in the folded condition, is heat sealed in this condition with the antileakage surface 24 facing up, and is thus secured.

Therefore, the shape of the flap 20 in the contacting portion 6 can be kept appropriately. Further, the side pocket 25 can be formed in a stable manner over the entire area of the portion, in which the central absorbent body 10 and the flap 20 contact with each other.

As the antileakage sheet, a sheet having been subjected to waterproof treatment, a liquid impermeable sheet, or the like, may be employed.

As an example of the sheet having been subjected to waterproof treatment, a nonwoven fabric treated with a water repellent oil agent, or the like, may be mentioned. As examples of the liquid impermeable sheet, a plastic sheet, such as a polyethylene sheet or a polypropylene sheet, a sheet obtained by carrying out a laminating process on a nonwoven fabric, and the like, may be mentioned.

The width V of each first flap 20a (shown in FIG. 29) should preferably fall within the range of 3 to 100 mm, and should more preferably fall within the range of 5 to 60 mm.

With the seventeenth embodiment of the sanitary napkin 1 having the structure described above, the antileakage surfaces 24, 24 can appropriately fit to the skin of the wearer, and leakage on both sides can be prevented effectively. Specifically, since the side pockets 25, 25 are formed, a discharged liquid flowing along the surface of the topsheet 11 flows into the side pockets 25, 25 and is thereafter absorbed by the absorbent member 13 from the side surfaces of the central absorbent body 10. Therefore, leakage on both sides can be prevented effectively. Also, the folding of the second flap 20b onto the absorbent member 13 can be carried out easily, and therefore the productivity can be kept high.

The eighteenth through twenty-first embodiments of the absorbent article in accordance with the present invention will be described hereinbelow with reference to FIGS. 30, 31, 32, and 33.

Figure 30:
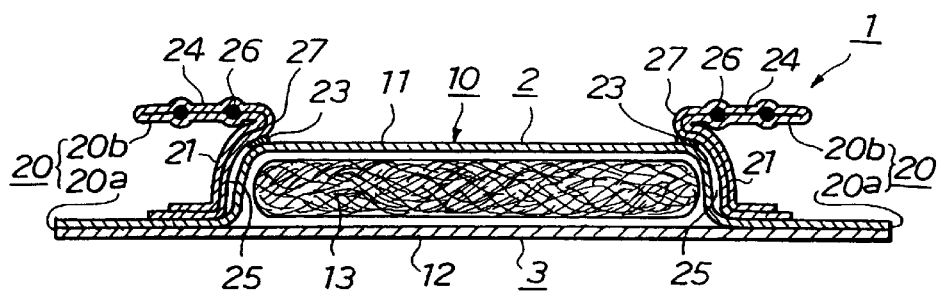
FIG. 30 is a sectional view showing an eighteenth embodiment of the absorbent article in accordance with the present invention, which is constituted as a sanitary napkin, the view corresponding to FIG. 29.
Figure 31:
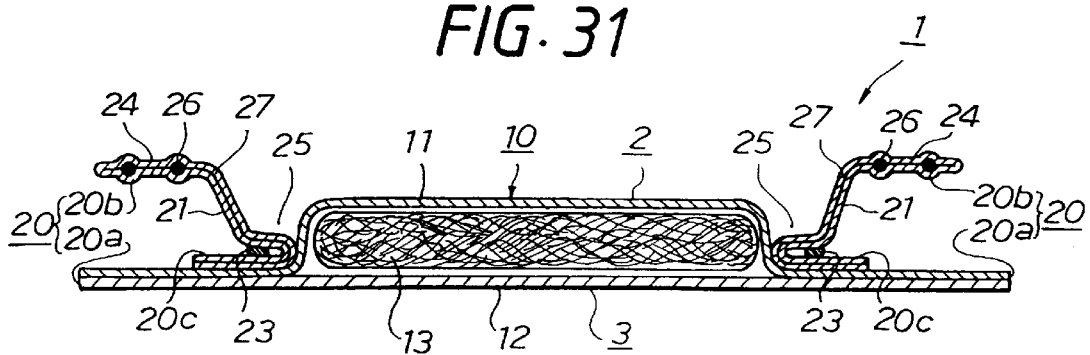
FIG. 31 is a sectional view showing a nineteenth embodiment of the absorbent article in accordance with the present invention, which is constituted as a sanitary napkin, the view corresponding to FIG. 29.
Figure 32:
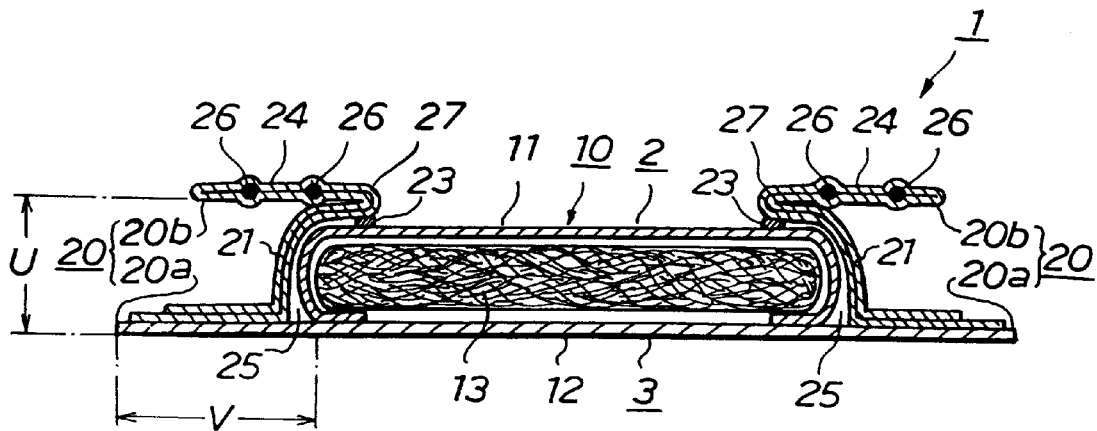
FIG. 32 is a sectional view showing a twentieth embodiment of the absorbent article in accordance with the present invention, which is constituted as a sanitary napkin, the view corresponding to FIG. 29.
Figure 33:
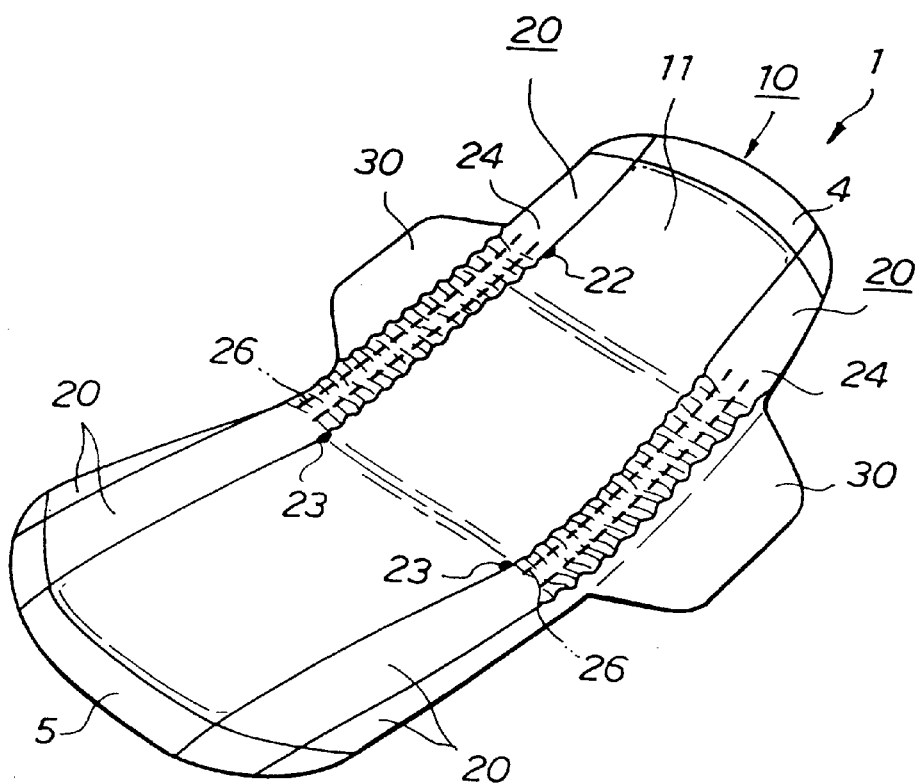
FIG. 33 is a perspective view showing a twenty-first embodiment of the absorbent article in accordance with the present invention, which is constituted as a sanitary napkin, the view corresponding to FIG. 26.

FIG. 30 is a sectional view showing the eighteenth embodiment of the absorbent article in accordance with the present invention, which is constituted as a sanitary napkin, the view corresponding to FIG. 29. FIG. 31 is a sectional view showing the nineteenth embodiment of the absorbent article in accordance with the present invention, which is constituted as a sanitary napkin, the view corresponding to FIG. 29. FIG. 32 is a sectional view showing the twentieth embodiment of the absorbent article in accordance with the present invention, which is constituted as a sanitary napkin, the view corresponding to FIG. 29. FIG. 33 is a perspective view showing the twenty-first embodiment of the absorbent article in accordance with the present invention, which is constituted as a sanitary napkin, the view corresponding to FIG. 26.

As for the eighteenth through twenty-first embodiments, only the features different from the aforesaid seventeenth embodiment will be described hereinbelow. As for the features which are not explained in the eighteenth through twenty-first embodiments, the explanation made for the aforesaid seventeenth embodiment is applied. In FIGS. 30, 31, 32, and 33, the same elements as in FIGS. 26 and 29 are numbered with the same reference numerals.

As illustrated in FIG. 30, in the eighteenth embodiment of the sanitary napkin 1, at the fixing portion 22, which is located in the front portion that is forward from the contacting portion 6, and at the fixing portion 23, which is located in the rear portion that is rearward from the contacting portion 6, the antileakage wall 21 is secured to the central absorbent body 10 at the side edge portions of the skin-contacting surface 2, i.e., to the vicinity of the side of the central absorbent body 10 at the skin-contacting surface 2.

As illustrated in FIG. 31, in the nineteenth embodiment of the sanitary napkin 1, at the fixing portion 22, which is located in the front portion that is forward from the contacting portion 6, and at the fixing portion 23, which is located in the rear portion that is rearward from the contacting portion 6, the antileakage wall 21 is secured to the surface formed by securing the lower portion of the second flap 20b to the first flap 20a. The side pocket 25 is thereby formed along each of the opposing longitudinal sides of the central absorbent body.

Since the nineteenth embodiment of the sanitary napkin 1 is constructed in the manner described above, larger side pockets 25, 25 can be formed. Therefore, the effects of preventing leakage on both sides can be enhanced.

As illustrated in FIG. 32, in the twentieth embodiment of the sanitary napkin 1, the first flap 20a is formed by only the extended portion of the backsheet 12.

Also, the topsheet 11 covers the side surfaces of the absorbent member 13 and the peripheral portion of the lower surface of the absorbent member 13 and is sealed with the backsheet 12 at the central absorbent body 10.

As illustrated in FIG. 33, in the twenty-first embodiment of the sanitary napkin 1, wing portions 30, 30, which have adhesive portions (not shown) for adhering to the underwear when the sanitary napkin 1 is used, are provided at the skin-uncontacting surface 3.

Each of the wing portions 30, 30 is formed by each of extended portions of the opposing lateral side edges of the first flaps 20a, 20a, which portion is extended outwardly from each edge of the opposing longitudinal sides of the central absorbent body 10 and corresponds to the contacting portion 6. Each of the adhesive portions is formed by applying an adhesive agent to each of the wing portions 30, 30 on the side of the skin-uncontacting surface 3. As the adhesive agent, any of known adhesive agents may be employed.

With the eighteenth through twenty-first embodiments, the same effects as those with the aforesaid seventeenth embodiment can be obtained.

The absorbent article in accordance with the present invention is not limited to the first through twenty-first embodiments described above and may be embodied in various other ways. For example, the constitutions described below may be employed.

Specifically, in the aforesaid embodiments of the sanitary napkin 1, in the front edge portion 4 and the rear edge portion 5 of the sanitary napkin 1, the folded flap 20 may be kept in the folded condition, may be heat sealed in this condition with the antileakage surface 24 facing up, and may thus be secured.

In this manner, the shape of the flap 20 in the contacting portion 6 can be kept appropriately. Further, the side pocket 25 can be formed in a stable manner over the entire area of the portion, in which the central absorbent body 10 and the flap 20 contact with each other.

As described above, in the front edge portion 4 and the rear edge portion 5 of the sanitary napkin 1, the folded flap 20 may be kept in the folded condition, may be heat sealed in this condition with the antileakage surface 24 facing up, and may thus be secured. In such cases, the fixing at the fixing portions 22, 22 in the front portion and the fixing at the fixing portions 23, 23 in the rear portion need not necessarily be carried out.

Also, in the embodiments described above, the antileakage wall 21 is secured to the topsheet 11 on the surface (i.e., the skin-contacting surface 2) of the central absorbent body 10. However, the present invention is not limited to such a constitution. For example, the antileakage wall 21 may be secured to the topsheet 11 at a side of the central absorbent body 10.

Further, in the embodiments described above, the antileakage wall 21 is secured to the central absorbent body 10 by the point-like fixing portions 22, 22, 23, 23. Alternatively, the antileakage wall 21 may be secured to the central absorbent body 10 by linear fixing portions (extending along the longitudinal direction of the absorbent article). In such cases, as in the fixing by the point-like fixing portions 22, 22, 23, 23, the fixing by the linear fixing portions may be carried out by using an adhesive agent, a heat sealing process, or the like. The lengths of the linear fixing portions may be selected arbitrarily. Also, at least either one of the linear fixing portions, which are formed in the front portion that is forward from the contacting portion 6, may not extend up to the front edge portion 4, and/or at least either one of the linear fixing portions, which are formed in the rear portion that is rearward from the contacting portion 6, may not extend up to the rear edge portion 5.

Furthermore, in the embodiments described above, the wing portions 30, 30 are formed at the positions corresponding to the contacting portion 6. However, no limitation is imposed on the positions of the wing portions 30, 30. For example, the positions of the wing portions 30, 30 may be shifted forwardly or rearwardly.

Moreover, the positions, at which the elastic members 26, 26 are located, are not limited to those in the embodiments described above. For example, the elastic members may be provided over the entire longitudinal area of the antileakage surface 24. Alternatively, the positions of the elastic members may be shifted forwardly or rearwardly.

Also, in the seventh through sixteenth embodiments described above, the constitutions described below may be employed.

Figure 18:
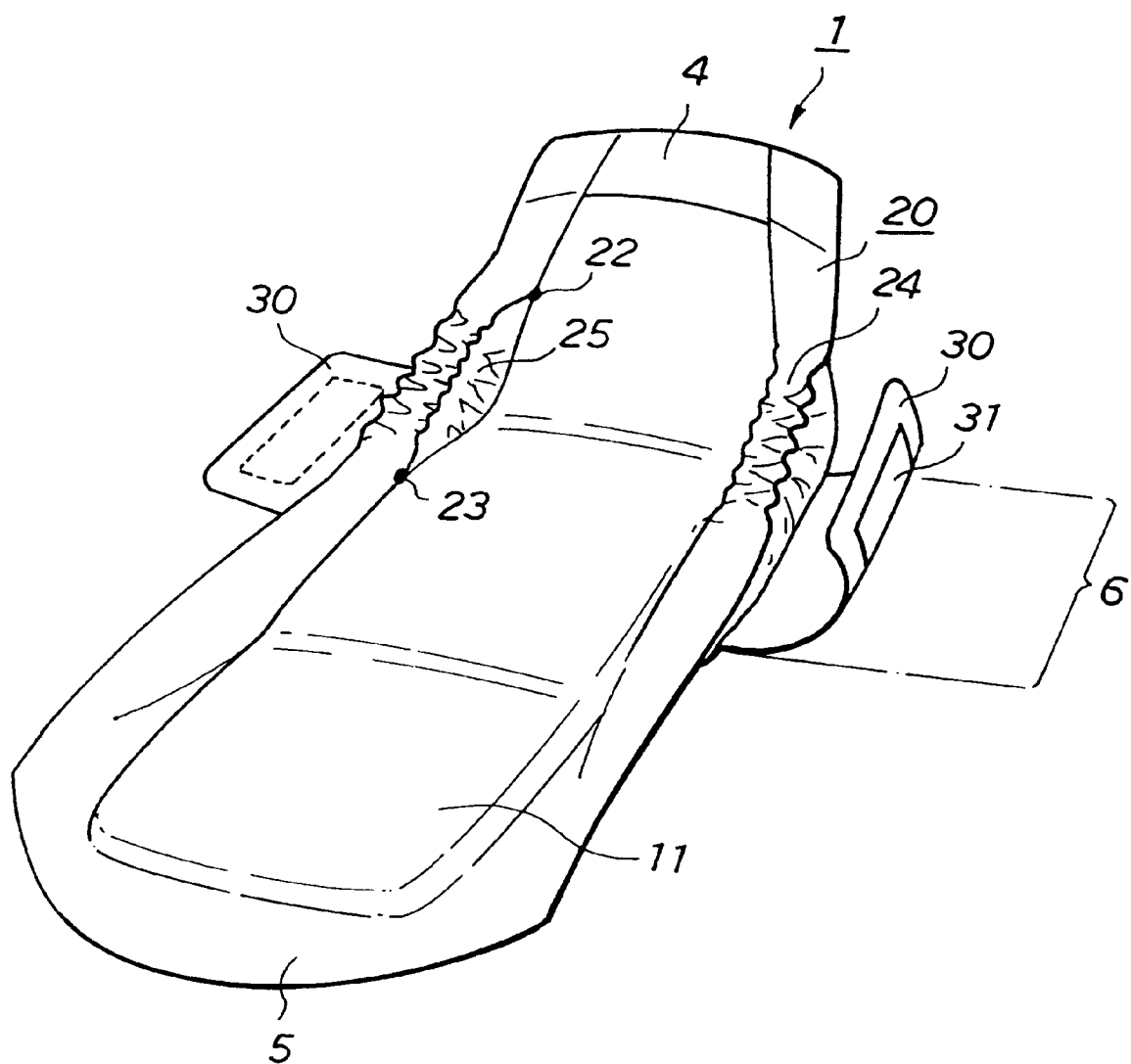
FIG. 18 is a perspective view showing another embodiment of the absorbent article in accordance with the present invention, the view corresponding to FIG. 11.

Specifically, as illustrated in FIG. 18, in the front edge portion 4 of the sanitary napkin 1, the folded flap 20 may be kept in the folded condition, may be heat sealed in this condition with the antileakage surface 24 facing up, and may thus be secured.

In this manner, the shape of the flap 20 in the contacting portion 6 can be kept appropriately. Further, the side pocket 25 can be formed in a stable manner over the entire area of the portion, in which the central absorbent body 10 and the flap 20 contact with each other.

In such cases, the fixing at the fixing portions 22, 22 in the front portion need not necessarily be carried out.

In the seventh embodiment shown in FIGS. 11 and 12, it is also possible to form the flap 20 by the backsheet 12 alone.

Also, in cases other than the cases where the wing portion 30 is combined with the backsheet 12 into an integral body as in the aforesaid eighth, ninth, and tenth embodiments shown in FIGS. 13, 14, and 15, the material for forming the wing portion 30 need not necessarily be impermeable to liquids. In such cases, the wing portion 30 may be constituted of a liquid permeable material, such as an ordinary nonwoven fabric or paper.

Further, in the sanitary napkins shown in FIGS. 13 and 14, in which the wing portion 30 is formed by the backsheet 12, it is possible to employ a backsheet formed by locating, at predetermined positions, a backsheet member for forming the backsheet portion located at the forward portion of the central absorbent body 10, a backsheet member for forming the backsheet portion located at the portion for forming the wing portion 30, and a backsheet member for forming the backsheet portion located at the rearward portion of the central absorbent body 10.

Furthermore, in the aforesaid thirteenth embodiment shown in FIGS. 19, 20, and 21, the flap 20 and the wing portion 30 are formed by the extended portion of the topsheet 11 and the extended portion of the backsheet 12. Alternatively, the flap 20 and the wing portion 30 may be formed by only either one of the extended portion of the topsheet 11 and the extended portion of the backsheet 12. In cases where the flap 20 and the wing portion 30 are formed by only the extended portion of the topsheet 11, when a nonwoven fabric is used as the topsheet 11, a nonwoven fabric, in which the portion for forming the flap 20 and the wing portion 30 has been subjected to a waterproof process, should preferably be employed. When a porous film is used as the topsheet 11, a porous film, in which the portion for forming the flap 20 and the wing portion 30 has no pore, should preferably be employed.

Also, in the aforesaid seventeenth embodiment shown in FIGS. 26, 27, 28, and 29, the constitutions described below may be employed.

Specifically, each of the flaps 20, 20 may not be secured in the front edge portion 4 and the rear edge portion 5. Instead, in the portion forward from the fixing portions 22, 22 in the front portion (i.e., in the portion which is located on the front side of the wearer when the sanitary napkin is used), the aforesaid folded condition of the flap 20 may be released gradually toward the front side in such a manner that the flap 20 takes a substantially flat surface-like shape. Similarly, in the portion rearward from the fixing portions 23, 23 in the rear portion (i.e., in the portion which is located on the rear side of the wearer when the sanitary napkin is used), the aforesaid folded condition of the flap 20 may be released gradually toward the rear side in such a manner that the flap 20 may take a substantially flat surface-like shape. In cases where the flap 20 is formed in this manner, the shape of the antileakage surface 24, which is substantially parallel to the skin-contacting surface 2, and the side pocket 25 can be formed and kept reliably.

Also, instead of the fixing being carried out in the contacting portion 6, the fixing described above may be carried out in the front portion and the rear portion of the sanitary napkin 1.

Furthermore, in the twenty-first embodiment shown in FIG. 33, the wing portions 30, 30 are formed at the positions corresponding to the contacting portion 6. However, no limitation is imposed on the positions of the wing portions 30, 30. For example, the positions of the wing portions 30, 30 may be shifted forwardly or rearwardly.

Further, the wing portion 30 may be formed by adhering the other sheet to the surface of the backsheet 12. In such cases, as the material for forming the other sheet, any of materials similar to the materials of the backsheet 12, the antileakage sheet, and the topsheet 11, and the like, may be employed.

While the slipping-off preventing agents 15, 15 are not shown in FIGS. 7 to 9 and FIGS. 11 to 33, the slipping-off preventing agents are provided on the skin-uncontacting surface 3 of the backsheet 12 of the sanitary napkins shown in FIGS. 7 to 9 and FIGS. 11 to 33 in the same manner as in the sanitary napkin shown in FIG. 2.

The absorbent article in accordance with the present invention is not limited to the sanitary napkin as in the embodiments described above and is also applicable to the other absorbent articles, for example, disposable diapers.

Many other variations and modifications of the invention will be apparent to those skilled in the art without departing from the spirit and scope of the invention. The above-described embodiments are, therefore, intended to be merely exemplary, and all such variations and modifications are intended to be included within the scope of the invention as defined in the appended claims.

What is claimed is:

1. An absorbent article having a central absorbent body comprising a liquid permeable topsheet, a liquid impermeable backsheet and an absorbent member interposed between the topsheet and the backsheet, and a pair of flaps defining both an antileakage surface portion and an antileakage wall portion provided along each edge of opposing longitudinal sides of said central absorbent body, wherein:

each of said flaps being connected to a noncontacting skin surface of the absorbent article which does not contact the skin of the wearer, each of said antileakage wall portions being adjacent to each edge of the opposing longitudinal sides of the central absorbent body wherein each of said antileakage wall portions and said edges of the opposing longitudinal sides of the central absorbent body form a side pocket, each side pocket includes fixing portions, each fixing portion secures a respective antileakage wall portion to a respective portion of said topsheet of said central absorbent body, each of said antileakage surface portions folding and extending outwardly and away from the central absorbent body, said antileakage surface portion which contacts the discharging area of the wearer in use is substantially parallel to the skin-contacting surface of the absorbent article, and when in use, each of said antileakage surface portions contacts the skin of the wearer, whereby said pockets substantially reduce leakage by containing discharged liquid flowing along and over a surface of said topsheet and permitting said longitudinal sides to absorb the contained liquid, said antileakage surface portions substantially increase fitting performance and comfort of said absorbent article relative to the wearer.

2. The absorbent article according to claim 1, wherein the antileakage wall is formed by folding each of the flaps toward the topsheet of the central absorbent body and secured by said fixing portions to the central absorbent body in a front portion and a rear portion of the discharging area of the wearer.

3. The absorbent article according to claim 2, wherein the antileakage surface is provided with an elastic member.

4. The absorbent article according to claim 2, wherein the flap is formed by sealing an extended portion of the topsheet and an extended portion of the backsheet.

5. The absorbent article according to claim 2, wherein the flap is formed by the topsheet or the backsheet.

6. The absorbent article according to claim 2, wherein the flap is formed by a sheet other than the topsheet and the backsheet, the sheet being waterproof or liquid impermeable.

7. The absorbent article according to claim 2, wherein wing portions for fixing the absorbent article in use are provided in such a manner that the wing portions are connected with the surface of the absorbent article which does not contact the skin along opposing longitudinal sides of the central absorbent body.

8. The absorbent article according to claim 7, wherein each of the wing portions is formed by each of extended portions of opposing lateral side edges of the backsheet, the extended portions corresponding to the portion which, in use, contacts the discharging area of the wearer.

9. The absorbent article according to claim 7, wherein the wing portion is adhered to the flap at a position slightly upper than the level of the surface of the absorbent article which, in use, does not contact the skin.

10. The absorbent article according to claim 2, wherein a wing portion for fixing the absorbent article in use is formed by extending the antileakage surface.

11. The absorbent article according to claim 1, wherein each flap comprises a first flap and a second flap, the first flap being formed by at least an extended portion of the backsheet, the second flap being formed by an antileakage sheet, the lower portion of the second flap being secured to the first flap, and the antileakage wall and the antileakage surface being formed by the second flap.

12. The absorbent article according to claim 11, wherein the antileakage surface is provided with an elastic member.

13. The absorbent article according to claim 11, wherein the antileakage wall, in the front portion, the rear portion or the front and rear portions of the discharging area of the wearer, is secured to the central absorbent body at the side edge portions of the surface of the absorbent article which, in use, does not contact the skin.

14. The absorbent article according to claim 11, wherein the antileakage wall, in the front portion, the rear portion, or the front and rear portions of the discharging area of the wearer, is secured to the surface formed by securing the lower portion of the second flap to the first flap.

15. The absorbent article according to claim 11, wherein the surface which, in use, contacts the skin of the wearer is provided with a wing portion having an adhesive portion for, in use, adhering the absorbent article and shorts.

16. The absorbent article according to claim 1, wherein said fixing portions are disposed at positions spaced from ends of said absorbent article and at ends of said pockets.

* * * * *